(12) United States Patent
McDonald et al.

(10) Patent No.: US 10,918,703 B2
(45) Date of Patent: Feb. 16, 2021

(54) FUSION PROTEINS FOR TREATING INFLAMMATORY DISEASES

(71) Applicant: THE REGENTS OF THE UNIVERSITY OF CALIFORNIA, Oakland, CA (US)

(72) Inventors: Karen A. McDonald, Fairfield, CA (US); Kalimuthu Karuppanan, Davis, CA (US); Carroll E. Cross, Davis, CA (US); Jason P. Eiserich, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/176,133

(22) Filed: Oct. 31, 2018

(65) Prior Publication Data

US 2019/0142914 A1    May 16, 2019

Related U.S. Application Data

(63) Continuation of application No. PCT/US2017/030627, filed on May 2, 2017.
(Continued)

(51) Int. Cl.
*A61K 38/55* (2006.01)
*A61P 9/10* (2006.01)
(Continued)

(52) U.S. Cl.
CPC ........... *A61K 38/55* (2013.01); *A61P 9/10* (2018.01); *A61P 9/14* (2018.01); *C07K 14/811* (2013.01);
(Continued)

(58) Field of Classification Search
None
See application file for complete search history.

(56) References Cited

U.S. PATENT DOCUMENTS

| | | |
|---|---|---|
| 5,734,014 A | 3/1998 | Ishima et al. |
| 8,674,178 B2 | 3/2014 | McDonald et al. |
| (Continued) | | |

FOREIGN PATENT DOCUMENTS

| | | |
|---|---|---|
| WO | 2011/107505 A1 | 9/2011 |
| WO | 2017192580 A1 | 11/2017 |

OTHER PUBLICATIONS

Yampolsky et al., The Exchangeability of Amino Acids in Proteins, Genetics, 2005, 170: 1459-1472 (Year: 2005).*
(Continued)

*Primary Examiner* — Julie Ha
*Assistant Examiner* — Kristina M Hellman
(74) *Attorney, Agent, or Firm* — Kilpatrick Townsend & Stockton LLP

(57) ABSTRACT

The present invention provides plant-made elafin-Fc fusion proteins for treating inflammatory diseases, e.g., inflammatory lung diseases. In certain embodiments, the fusion proteins comprise one or more point mutations, which confer improved properties, such as increased resistance to oxidation, cleavage, and increased half-life. The present invention additionally provides polynucleotides encoding the fusion proteins, recombinant cells and expression vectors, and transgenic plants comprising the fusion protein coding sequences. The present invention further provides methods for the production of the fusion proteins.

14 Claims, 11 Drawing Sheets

Specification includes a Sequence Listing.

Gene design for elafin-Fc

Related U.S. Application Data

(60) Provisional application No. 62/330,717, filed on May 2, 2016.

(51) Int. Cl.
  *A61P 9/14* (2006.01)
  *C07K 14/81* (2006.01)
  *C12N 15/82* (2006.01)
  *C07K 19/00* (2006.01)

(52) U.S. Cl.
  CPC .......... *C07K 19/00* (2013.01); *C12N 15/8205* (2013.01); *C12N 15/8243* (2013.01); *C12N 15/8257* (2013.01); *C12N 15/8258* (2013.01); *C07K 2319/30* (2013.01)

(56) References Cited

U.S. PATENT DOCUMENTS

| | | |
|---|---|---|
| 2010/0281567 A1 | 11/2010 | Galili et al. |
| 2012/0045818 A1 | 2/2012 | Hwang et al. |
| 2013/0011399 A1* | 1/2013 | Timmer ............... C07K 16/241 424/134.1 |
| 2016/0017019 A1 | 1/2016 | Ilan et al. |
| 2016/0024179 A1 | 1/2016 | Warner et al. |

OTHER PUBLICATIONS

Hristodorov et al., "With or Without Sugar? (A)glycosylation of Therapeutic Antibodies," Mol. Biotechnol. 54:1056-1068 (2013) (Year: 2013).*

Strasser, "Engineering of Human-Type O-Glycosylation in *Nicotiana benthamiana* Plants", Bioengineered, vol. 4, No. 4, Jul.-Aug. 2013, pp. 191-196.

Agarwal et al., "Expression of modified gene encoding functional human α-1-antitrypsin protein in transgenic tomato plants", Transgenic Res, 2008, vol. 17, pp. 881-896.

An et al., "Organ-Specific and Developmental regulation of the nopaline synthase promoter in transgenic tobacco plants" Plant Physiol, 1988, vol. 88, pp. 547-552.

Anthony et al., "Intravenous gammaglobulin suppresses inflammation through a novel T(H)2 pathway" Nature, 2011, vol. 475, pp. 110-113.

Arjmand et al., "Expression and Purification of Functionally Active Recombinant Human Alpha 1-Antitrypsin in Methylotrophic Yeast *Pichia pastoris*", Avicenna J Med Biotechnol, 2011, vol. 3, pp. 127-134.

Arzola et al., "Transient co-expression of post-transcriptional gene silencing suppressors for increased in planta expression of a recombinant anthrax receptor fusion protein", International Journal of Molecular Sciences , 2011, vol. 12, pp. 4975-4990.
ATS Board of Directors and ERS Executive Committee, "American Thoracic Society/European Respiratory Society statement: standards for the diagnosis and management of individuals with alpha-1 antitrypsin deficiency", Am J Respir Crit Care Med, Feb. 2003, vol. 168, pp. 818-900.
Ausubel et al, "Current Protocols in Molecular Biology" Current Protocols, a joint venture between Greene Publishing Associates, Inc. and John Wiley & Sons, Inc., (supplemented through 2007), pp. 1-4648.
Bakker et al., "An antibody produced in tobacco expressing a hybrid β 1,4-galactosyltransferase is essentially devoid of plant carbohydrate epitopes", Proc. Natl. Acad. Sci. USA, May 16, 2006, vol. 103, No. 20, pp. 7577-7582.
Batzer et al., "Enhanced evolutionary PCR using oligonucleotides with inosine at the 3'-terminus" Nucleic Acids Research, 1991, vol. 19 No. 18, p. 5081.
Beck et al., "Therapeutic Fc-fusion proteins and peptides as successful alternatives to antibodies", MAbs 2011, vol. 3, pp. 415-416.
Bischoff et al., "Purification and biochemical characterization of recombinant α1-antitrypsin variants expressed in *Escherichia coli*", Biochemistry, 1991, vol. 30:3464-3472.
Bourbonnais et al., "Production of full-length human pre-elafin, an elastase specific inhibitor, from yeast requires the absence of a functional yapsin 1 (Yps1p) endoprotease", Protein Expression and Purification, 2000, vol. 20, pp. 485-491.
Cassol et al., "Rapid DNA fingerprinting to control for specimen errors in HIV testing by the polymerase chain reaction", Molecular and Cellular Probes, 1992, vol. 6, pp. 327-331.
Castilho et al., "In planta protein sialylation through overexpression of the respective mammalian pathway", The Journal of Biological Chemistry, May 21, 2010, vol. 285, pp. 15923-15930.
Corbacho et al., "Compromised aortic vasoreactivity in male estrogen receptor-α-deficient mice during acute lipopolysaccharide-induced inflammation", Endocrinology, 2007, vol. 148, pp. 1403-1411.
Czajkowsky et al., "Fc-fusion proteins: new developments and future perspectives", EMBO Mol Med, 2012, vol. 4, pp. 1015-1028.
Devereux et al., "A comprehensive set of sequence analysis programs for the VAX", Nucl. Acid Res., 1984, vol. 12, pp. 387-395.
Fromm et al., "An octopine synthase enhancer element directs tissue-specific expression and binds ASF-1, a factor from tobacco nuclear extracts", Plant Cell, 1989, vol. 1, pp. 977-984.
Grevys et al., "Fc Engineering of Human IgG1 for Altered Binding to the Neonatal Fc Receptor Affects Fc Effector Functions", The Journal of Immunology, 2015, vol. 194, pp. 5497-5508.
Griese et al., "α1-Antitrypsin inhalation reduces airway inflammation in cystic fibrosis patients", Eur Respir J, 2007, vol. 29, No. 2, pp. 240-250.
Griffiths et al. "Relationship between Protein Structure and Methionine Oxidation in Recombinant Human α1-Antitrypsin" Biochemistry, 2002, vol. 41, pp. 6245-6252.
Guyot et al., "Elafin, an elastase-specific inhibitor, is cleaved by its cognate enzyme neutrophil elastase in sputum from individuals with cystic fibrosis", J Biol Chem, 2008, vol. 283, pp. 32377-32385.
Guyot et al., "Functional study of elafin cleaved by Pseudomonas aeruginosa metalloproteinases", Biol Chem., Jun. 2010, vol. 391, pp. 705-716.
Hemsley et al., "A simple method for site-directed mutagenesis using the polymerase chain reaction" Nucleic Acids Res, 1989, vol. 17, No. 16, pp. 6545-6551.
Ho et al., "Site-directed mutagenesis by overlap extension using the polymerase chain reaction" Gene, 1989, vol. 77 (1), pp. 51-59.
Huang et al., "Chemoenzymatic Glycoengineering of Intact IgG Antibodies for Gain of Functions", Journal of American Chemical Society, 2012, vol. 134, pp. 12308-12318.
Huether et al., "Glyco-engineering of moss lacking plant-specific sugar residues", Plant Biol., 2005, vol. 7 (3), pp. 292-299.
Kaneko et al., "Anti-Inflammatory Activity of Immunoglobulin G Resulting from Fc Sialylation" Science Report, Aug. 4, 2006, vol. 313, pp. 670-673.
Karsten et al., "Galactysylated IgG1 links FcyRIIB and Dectin-1 to block complement-mediated inflammation", Nature Medicine, 2012, vol. 18, No. 9, pp. 1401-1406.
Karuppanan et al., "Expression, Purification, and Biophysical Characterization of a Secreted Anthrax Decoy Fusion Protein in Nicotiana benthamiana", International Journal of Molecular Science, 2017, 18, p. 1-13.
Kobayashi et al., "A single dose of lipopolysaccharide into mice with emphysema mimics human chronic obstructive pulmonary disease exacerbation as assessed by micro-computed tomography", Am J Respir Cell Mol Biol, 2013, vol. 49, pp. 971-977.
Kremserova et al., "Lung neutrophilia in myeloperoxidase deficient mice during the course of acute pulmonary inflammation" Oxidative Medicine and Cellular Longevity, 2016, pp. 1-14.
Kultz et al., "Quantitative Molecular Phenotyping of Gill Remodeling in a Cichlid Fish Responding to Salinity Stress" Mol Cell Proteomics, 2013, vol. 12, pp. 3962-3975.
Kumpalume et al., "New process for the manufacture of α-1 antitrypsin" J Chromatogr A, 2007, vol. 1148, pp. 31-37.

(56) References Cited

OTHER PUBLICATIONS

Lauer et al., "Generation of a novel proteolysis resistant vascular endothelial growth factor165 variant by a site-directed mutation at the plasmin sensitive cleavage site", FEBS Letters 531, 2002, pp. 309-313.
Lucas et al., "Targeting COPD: Advances on Low-Molecular-Weight Inhibitors of Human Neutrophil Elastase", Med Res Rev, 2013, vol. 33, No. S1, pp. E73-E101.
Maier et al., "Analysis of methionine sulfoxide in proteins", Methods Enzymolology, 1995, vol. 251, pp. 455-461.
Medi-Span Price Rx, http://www.wolterskluwercdi.com/price-rx/, p. 1-3, retrieved Aug. 2020.
Mitsunaga et al., "Sequence-specific interactions of a nuclear protein factor with the promoter region of a rice gene for α-amylase, RAmy3D", Nucleic Acids Research, 1994, vol. 11, pp. 1948-1952.
Nandi et al., "Techno-economic analysis of a transient plant-based platform for monoclonal antibody production" MABS, 2016, vol. 8, No. 8, pp. 1456-1466.
Needieman & Wunsch, "A general method applicable to the search for similarities in the amino acid sequence of two proteins", J. MoL, Biol., 1970, vol. 48, pp. 443-453.
Nobar et al., "Oxidized elafin and trappin poorly inhibit the elastolytic activity of neutrophil elastase and proteinase 3", FEBS Journal, 2005, vol. 272, pp. 5883-5893.
Nowak et al., "Nicotine inhibits α-1-proteinase inhibitor inactivation by oxidants derived from human polymorphonuclear leukocytes", Abstract from Experimental Pathology, 1990, vol. 38, pp. 249-255.
Ochman et al., "Genetic applications of an inverse polymerase chain reaction" Genetics, 1988, vol. 120 (3), pp. 621-623.
Odel et al., "Identification of DNA sequences required for activity of the cauliflower mosaic virus 35S promoter", Letters to Nature, 1985, vol. 313, pp. 810-812.
Ohtsuka et al., "An Alternative Approach to Deoxyoligonucleotides as Hybridization Probes by Insertion of Deoxyinosine at Ambiguous Codon Positions", The Journal of Biological Chemistry, 1985, vol. 260, pp. 2605-2608.
Palacpac et al., "Stable expression of human β1,4-galactosyltransferase in plant cells modifies N-linked glycosylation patterns", Proc. Natl Acad. Sci. USA, Apr. 1999, vol. 96 (8), pp. 4692-4697.
Pearson & Lipman, "Improved tools for biological sequence comparison" Proc. Natl. Acad. Sci. USA, 1988, vol. 85, pp. 2444-2448.
Proteo Inc., "Proteo, Inc. /Proteo Biotech AG: FDA Grants Orphan Drug Designation to Elafin for Prevention of Inflammatory Complications of Transthoracic Esophagectomy", 2013, pp. 1-2.
Rossolini et al., "Use of deoxyinosine-containing primers vs degenerate primers for polymerase chain reaction based on ambiguous sequence information", Mol. Cell. Probes, 1994, vol. 8, pp. 91-98.
Schahs et al. "Production of a monoclonal antibody in plants with a humanized N-glycosylation pattern", Plant Biotechnology Journal, 2007, vol. 5 (5), pp. 657-663.
Schmelzer et al., "Soluble epoxide hydrolase is a therapeutic target for acute inflammation", The National Academy of Sciences of the USA, Apr. 25, 2005, vol. 102, pp. 9772-9777.
Shamloul et al. "Optimization and utilization of Agrobacterium-mediated transient protein production in Nicotiana", J Vis Exp., Apr. 19, 2014, pp. 1-13.

Shaw et al., "Therapeutic potential of human elafin" Biochem Soc Trans, 2011, vol. 39, pp. 1450-1454.
Sheludko "Agrobacterium-mediated transient expression as an approach to production of recombinant proteins in plants", Recent Pat Biotechnol, 2008, vol. 2, pp. 198-208.
Silberstein et al., 2016, Plant based production, purification and characterization of oxidation resistant alpha-1 antitrypsin In: Davies KJ, editor. SfRBM's 23 Annual meeting Los Angeles, CA, USA: Free radical biology & medicne pp. S59-S60.
Simpson et al., "Adenoviral augmentation of elafin protects the lung against acute injury mediated by activated neutrophils and bacterial infection" J Immunol, 2001, vol. 167, pp. 1778-1786.
Small et al., "A Functional Variant of Elafin With Improved Anti-Inflammatory Activity for Pulmonary Inflammation", Molecular therapy, Jan. 2015, vol. 23, No. 1, pp. 24-31.
Smith & Waterman "Comparison of Biosequences", Advances in Applied Mathmatics, 1981, vol. 2, pp. 482-489.
Stoller et al., "A review of α1-antitrypsin deficiency" Am J Respir Crit Care Med, Feb. 1, 2012, vol. 185, pp. 246-259.
Stoller et al., Alpha-1 Antitrypsin Deficiency, GeneReviews, available at http://www.ncbi.nlm.nih.gov/books/NBK1519/, pp. 1-24.
Strasser et al., "Generation of glyco-engineered Nicotiana benthamiana for the production of monoclonal antibodies with a homogeneous human-like N-glycan structure", Plant Biotechnology Journal, 2008, vol. 6 (4), pp. 392-402.
Strum et al., "Automated Assignments of N- and O-Site Specific Glycosylation with Extensive Glycan Heterogeneity of Glycoprotein Mixtures" Analytical Chemistry, 2013, vol. 85, pp. 5666-5675.
"Suppressor of RNA silencing", http://viralzone.expasy.org/all_by_protein/891.html, pp. 1-4, retrieved Aug. 2020.
Taggart et al., "Oxidation of either methionine 351 or methionine 358 in α1-antitrypsin causes loss of anti-neutrophil elastase activity" J Biol Chem, 2000, vol. 275, pp. 1-44.
Takaya et al., "Importance of dissolution process on systemic availability of drugs delivered by colon delivery system", Journal of Control Release, 1998, vol. 50, pp. 111-122.
Tonelli et al., "Augmentation therapy in alpha-1 antitrypsin deficiency: advances and controversies", Therapeutic Advances in Respiratory Disease, 2010, vol. 4, pp. 289-312.
Wang et al., "Use of a Soluble Epoxide Hydrolase Inhibitor in Smoke-Induced Chronic Obstructive Pulmonary Disease", Am J Respir Cell Mol Biol, 2012, vol. 46, pp. 614-622.
Weldon et al., "Decreased levels of secretory leucoprotease inhibitor in the Pseudomonas-infected cystic fibrosis lung are due to neutrophil elastase degradation", Journal of Immunology, 2009, vol. 183, pp. 8148-8156.
Wilken et al., "Recovery and purification of plant-made recombinant proteins", Biotechnology Advances, 2012, vol. 30, pp. 419-433.
Zalevsky et al., "Enhanced antibody half-life improves in vivo activity" Nature Biotechnology, Feb. 2010, vol. 28, No. 2, pp. 157-159.
Zhou "Determining protein half-lives", Methods Mol. Biol., 2004, vol. 284, pp. 67-77.
Zoller, Mark J., "New molecular biology methods for protein engineering" Current Opinion in Biotechnology, 1991, vol. 2 (4), pp. 526-531.

* cited by examiner

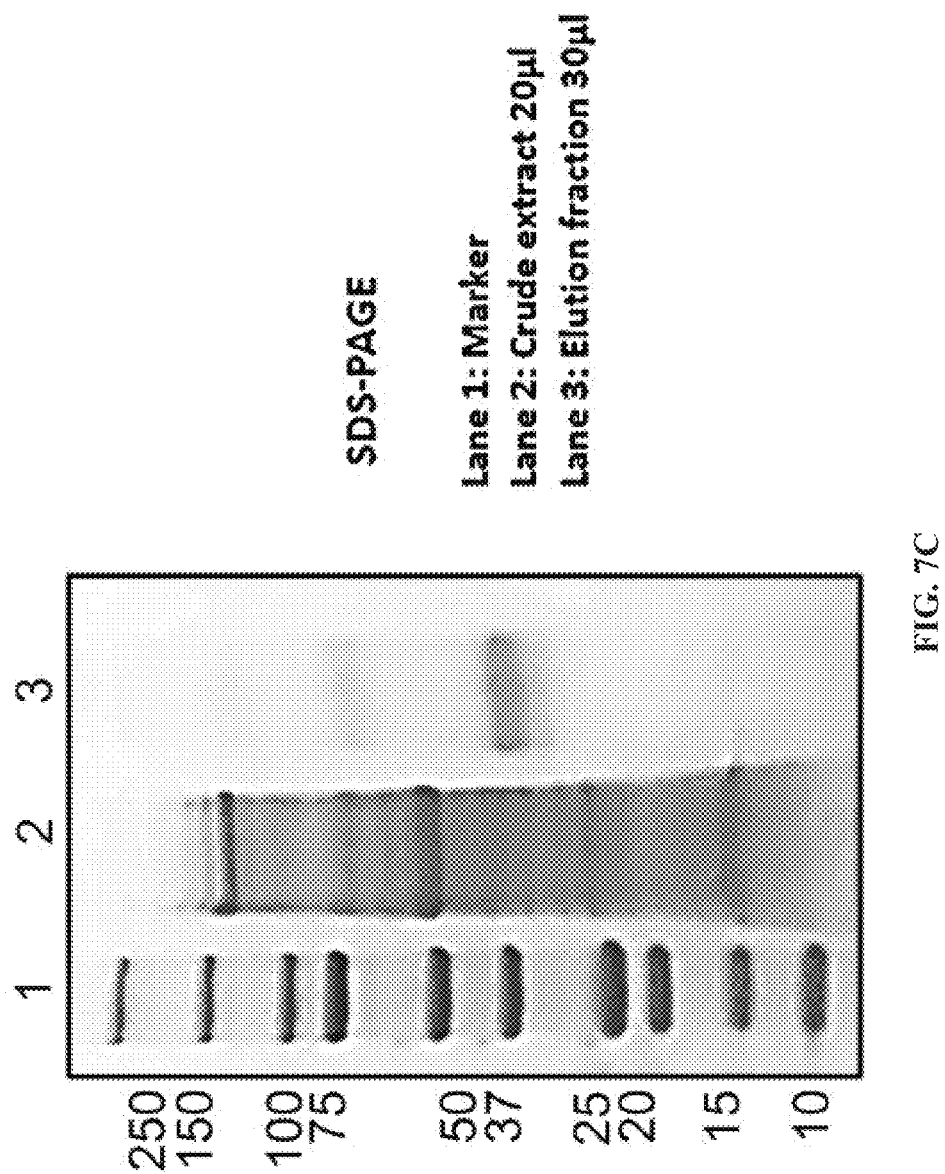

SEQUENCE LISTING

<160> NUMBER OF SEQ ID NOS: 16

<210> SEQ ID NO 1
<211> LENGTH: 57
<212> TYPE: PRT
<213> ORGANISM: Homo sapiens

<400> SEQUENCE: 1

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
            20                  25                  30

Leu Lys Asp Thr Asp Cys Pro Gly Ile Lys Lys Cys Cys Glu Gly Ser
        35                  40                  45

Cys Gly Met Ala Cys Phe Val Pro Gln
    50                  55

<210> SEQ ID NO 2
<211> LENGTH: 25
<212> TYPE: PRT
<213> ORGANISM: Oryza sativa

<400> SEQUENCE: 2

Met Lys Asn Thr Ser Ser Leu Cys Leu Leu Leu Val Val Leu Cys
1               5                   10                  15

Ser Leu Thr Cys Asn Ser Gly Gln Ala
            20                  25

<210> SEQ ID NO 3
<211> LENGTH: 10
<212> TYPE: PRT
<213> ORGANISM: Homo sapiens

<400> SEQUENCE: 3

Glu Pro Lys Ser Cys Asp Lys Thr His Thr
1               5                   10

<210> SEQ ID NO 4
<211> LENGTH: 222
<212> TYPE: PRT
<213> ORGANISM: Homo sapiens

```
<400> SEQUENCE: 4

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 5
<211> LENGTH: 314
<212> TYPE: PRT
<213> ORGANISM: Artificial Sequence
<220> FEATURE:
<223> OTHER INFORMATION: Synthetic Construct

<400> SEQUENCE: 5

Met Lys Asn Thr Ser Ser Leu Cys Leu Leu Leu Val Val Leu Cys
1               5                   10                  15

Ser Leu Thr Cys Asn Ser Gly Gln Ala Ala Gln Glu Pro Val Lys Gly
            20                  25                  30

Pro Val Ser Thr Lys Pro Gly Ser Cys Pro Ile Ile Leu Ile Arg Cys
        35                  40                  45

Ala Met Leu Asn Pro Pro Asn Arg Cys Leu Lys Asp Thr Asp Cys Pro
    50                  55                  60

Gly Ile Lys Lys Cys Cys Glu Gly Ser Cys Gly Met Ala Cys Phe Val
65                  70                  75                  80

Pro Gln Glu Pro Lys Ser Cys Asp Lys Thr His Thr Cys Pro Pro Cys
                85                  90                  95

Pro Ala Pro Glu Leu Leu Gly Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
```

-continued

```
                130                 135                 140
Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
                180                 185                 190

Lys Ala Leu Pro Ala Pro Ile Glu Lys Thr Ile Ser Lys Ala Lys Gly
                195                 200                 205

Gln Pro Arg Glu Pro Gln Val Tyr Thr Leu Pro Pro Ser Arg Asp Glu
                210                 215                 220

Leu Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
                260                 265                 270

Leu Tyr Ser Lys Leu Thr Val Asp Lys Ser Arg Trp Gln Gln Gly Asn
                275                 280                 285

Val Phe Ser Cys Ser Val Met His Glu Ala Leu His Asn His Tyr Thr
290                 295                 300

Gln Lys Ser Leu Ser Leu Ser Pro Gly Lys
305                 310
```

<210> SEQ ID NO 6
<211> LENGTH: 314
<212> TYPE: PRT
<213> ORGANISM: Artificial Sequence
<220> FEATURE:
<223> OTHER INFORMATION: Synthetic Construct

<400> SEQUENCE: 6

```
Met Lys Asn Thr Ser Ser Leu Cys Leu Leu Leu Val Val Leu Cys
1               5                   10                  15

Ser Leu Thr Cys Asn Ser Gly Gln Ala Ala Gln Glu Pro Gly Lys Gly
                20                  25                  30

Pro Gly Ser Thr Lys Pro Gly Ser Cys Pro Ile Ile Leu Ile Arg Cys
                35                  40                  45

Ala Leu Leu Asn Pro Pro Asn Arg Cys Leu Lys Asp Thr Asp Cys Pro
                50                  55                  60

Gly Ile Lys Lys Cys Cys Glu Gly Ser Cys Gly Val Ala Cys Phe Val
65                  70                  75                  80

Pro Gln Glu Pro Lys Ser Cys Asp Lys Thr His Thr Cys Pro Pro Cys
                85                  90                  95

Pro Ala Pro Glu Leu Leu Gly Gly Pro Ser Val Phe Leu Phe Pro Pro
                100                 105                 110

Lys Pro Lys Asp Thr Leu Met Ile Ser Arg Thr Pro Glu Val Thr Cys
                115                 120                 125

Val Val Val Asp Val Ser His Glu Asp Pro Glu Val Lys Phe Asn Trp
                130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
```

```
            180                 185                 190
Lys Ala Leu Pro Ala Pro Ile Glu Lys Thr Ile Ser Lys Ala Lys Gly
                195                 200                 205

Gln Pro Arg Glu Pro Gln Val Tyr Thr Leu Pro Pro Ser Arg Asp Glu
    210                 215                 220

Leu Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 7
<211> LENGTH: 314
<212> TYPE: PRT
<213> ORGANISM: Artificial Sequence
<220> FEATURE:
<223> OTHER INFORMATION: Synthetic Construct

<400> SEQUENCE: 7

Met Lys Asn Thr Ser Ser Leu Cys Leu Leu Leu Val Val Leu Cys
1               5                   10                  15

Ser Leu Thr Cys Asn Ser Gly Gln Ala Ala Gln Glu Pro Gly Lys Gly
                20                  25                  30

Pro Gly Ser Thr Lys Pro Gly Ser Cys Pro Ile Ile Leu Ile Arg Cys
            35                  40                  45

Ala Leu Leu Asn Pro Pro Asn Arg Cys Leu Lys Asp Thr Asp Cys Pro
        50                  55                  60

Gly Ile Lys Lys Cys Cys Glu Gly Ser Cys Gly Val Ala Cys Phe Val
65                  70                  75                  80

Pro Gln Glu Pro Lys Ser Cys Asp Lys Thr His Thr Cys Pro Pro Cys
                85                  90                  95

Pro Ala Pro Glu Leu Leu Gly Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
    130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Asp Glu
    210                 215                 220

Leu Thr Lys Asn Gln Val Ser Leu Thr Cys Leu Val Lys Gly Phe Tyr
```

```
                225                 230                 235                 240
Pro Ser Asp Ile Ala Val Glu Trp Glu Ser Asn Gly Gln Pro Glu Asn
                    245                 250                 255

Asn Tyr Lys Thr Thr Pro Pro Val Leu Asp Ser Asp Gly Ser Phe Phe
                260                 265                 270

Leu Tyr Ser Lys Leu Thr Val Asp Lys Ser Arg Trp Gln Gln Gly Asn
            275                 280                 285

Val Phe Ser Cys Ser Val Leu His Glu Ala Leu His Ser His Tyr Thr
        290                 295                 300

Gln Lys Ser Leu Ser Leu Ser Pro Gly Lys
305                 310
```

<210> SEQ ID NO 8
<211> LENGTH: 942
<212> TYPE: DNA
<213> ORGANISM: Artificial Sequence
<220> FEATURE:
<223> OTHER INFORMATION: Synthetic Construct

<400> SEQUENCE: 8

```
atgaagaata cttcttcact ttgtcttttg cttttggttg ttctttgttc attgacatgc    60
aattctggtc aagctgctca ggaacctgtt aagggtccag tttcaactaa acctggatct   120
tgtccaatta ttcttatcag atgcgctatg ttgaatcctc aaataggtg tttgaaggat    180
acagattgcc ctggaattaa gaatgttgc gaaggttcat gtggaatggc ttgctttgtt    240
cctcaagagc caaagtcttg tgataaaact catacatgtc ctccatgccc tgctccagag   300
cttttgggtg gaccttctgt ttttcttttt cctccaaagc caaagatac tttgatgatt    360
tcaagaactc ctgaagttac atgcgttgtt gttgatgttt ctcatgaaga tccagaggtt   420
aagtttaatt ggtatgttga tggtgttgag gttcataatg ctaagacaaa accaagagaa   480
gagcaatata attcaactta cagggttgtt tctgttctta cagttttgca tcaggattgg   540
cttaatggta agagtacaa gtgtaaagtt tcaaataagg ctttgcctgc tccaatcgaa    600
aagactattt ctaaggctaa aggacaacct agagagccac aggtttatac acttcctcca   660
tcaagggatg aattgactaa gaaccaagtt tctcttacat gcttggttaa aggtttttac   720
ccttcagata ttgctgttga atgggagtct aatggtcagc cagaaaataa ctataagact   780
acacctccag ttcttgattc agatggttct ttctttcttt actcaaagtt gactgttgat   840
aagtctaggt ggcaacaggg aaatgttttc tcttgttcag ttatgcatga ggctttgcat   900
aaccattaca cacagaagtc tctttcattg tctcctggaa aa                      942
```

<210> SEQ ID NO 9
<211> LENGTH: 942
<212> TYPE: DNA
<213> ORGANISM: Artificial Sequence
<220> FEATURE:
<223> OTHER INFORMATION: Synthetic Construct

<400> SEQUENCE: 9

```
atgaagaata cttcttcact ttgtcttttg cttttggttg ttctttgttc attgacatgc    60
aattctggac aagctgctca ggaacctgga aagggaccag gttcaactaa acctggttct   120
tgtccaatta ttcttatcag atgcgctctt ttgaatcctc aaataggtg tttgaaggat    180
acagattgcc ctggaattaa gaatgttgc gaaggtcat gtggtgttgc ttgctttgtt     240
cctcaagagc caaagtcttg tgataaaact catacatgtc ctccatgccc tgctccagag   300
```

| | | |
|---|---|---|
| cttttgggtg gaccttctgt ttttcttttt cctccaaagc caaagatac tttgatgatt | 360 | |
| tcaagaactc ctgaagttac atgcgttgtt gttgatgttt ctcatgaaga tccagaggtt | 420 | |
| aagtttaatt ggtatgttga tggtgttgag gttcataatg ctaagacaaa accaagagaa | 480 | |
| gagcaatata attcaactta cagggttgtt tctgttctta cagttttgca tcaggattgg | 540 | |
| cttaatggta aagagtacaa gtgtaaagtt tcaaataagg ctttgcctgc tccaatcgaa | 600 | |
| aagactattt ctaaggctaa aggtcaacct agagagccac aggtttatac acttcctcca | 660 | |
| tcaagggatg aattgactaa gaaccaagtt tctcttacat gcttggttaa aggattttac | 720 | |
| ccttcagata ttgctgttga atgggagtct aatggtcagc cagaaaataa ctataagact | 780 | |
| acacctccag ttcttgattc agatggttct ttctttcttt actcaaagtt gactgttgat | 840 | |
| aagtctaggt ggcaacaggg taatgttttc tcttgttcag ttatgcatga ggctttgcat | 900 | |
| aaccattaca cacagaagtc tctttcattg tctcctggaa aa | 942 | |

<210> SEQ ID NO 10
<211> LENGTH: 942
<212> TYPE: DNA
<213> ORGANISM: Artificial Sequence
<220> FEATURE:
<223> OTHER INFORMATION: Synthetic Construct

<400> SEQUENCE: 10

| | | |
|---|---|---|
| atgaagaata cttcttcact ttgtcttttg cttttggttg ttctttgttc attgacatgc | 60 | |
| aattctggac aagctgctca ggaacctgga aagggaccag gttcaactaa acctggttct | 120 | |
| tgtccaatta ttcttatcag atgcgctctt ttgaatcctc caaataggtg tttgaaggat | 180 | |
| acagattgcc ctggaattaa gaaatgttgc gaaggatcat gtggtgttgc ttgctttgtt | 240 | |
| cctcaagagc caaagtcttg tgataaaact catacatgtc ctccatgccc tgctccagag | 300 | |
| cttttgggtg gaccttctgt ttttcttttt cctccaaagc caaagatac tttgatgatt | 360 | |
| tcaagaactc ctgaagttac atgcgttgtt gttgatgttt ctcatgaaga tccagaggtt | 420 | |
| aagtttaatt ggtatgttga tggtgttgag gttcataatg ctaagacaaa accaagagaa | 480 | |
| gagcaatata attcaactta cagggttgtt tctgttctta cagttttgca tcaggattgg | 540 | |
| cttaatggta aagagtacaa gtgtaaagtt tcaaataagg ctttgcctgc tccaatcgaa | 600 | |
| aagactattt ctaaggctaa aggtcaacct agagagccac aggtttatac acttcctcca | 660 | |
| tcaagggatg aattgactaa gaaccaagtt tctcttacat gcttggttaa aggattttac | 720 | |
| ccttcagata ttgctgttga atgggagtct aatggtcagc cagaaaataa ctataagact | 780 | |
| acacctccag tttttggattc agatggttct ttctttcttt actcaaagtt gactgttgat | 840 | |
| aagtctaggt ggcaacaggg taatgttttc tcttgttcag ttcttcatga ggctttgcat | 900 | |
| tctcattata cacagaagtc tctttcattg tctcctggaa aa | 942 | |

<210> SEQ ID NO 11
<211> LENGTH: 171
<212> TYPE: DNA
<213> ORGANISM: Artificial Sequence
<220> FEATURE:
<223> OTHER INFORMATION: Synthetic Construct

<400> SEQUENCE: 11

| | | |
|---|---|---|
| gcccaagaac cagtcaaggg tccagtcagt acaaagccag gtagttgccc aattatcctt | 60 | |
| attagatgtg ccatgttgaa tcctcctaac agatgtttga aggatactga ttgccctgga | 120 | |
| atcaaaaagt gctgtgaagg tagttgcggt atggcttgtt tcgtccctca g | 171 | |

<210> SEQ ID NO 12
<211> LENGTH: 57
<212> TYPE: PRT
<213> ORGANISM: Artificial Sequence
<220> FEATURE:
<223> OTHER INFORMATION: Synthetic Construct

<400> SEQUENCE: 12

```
Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
            20                  25                  30

Leu Lys Asp Thr Asp Cys Pro Gly Ile Lys Lys Cys Cys Glu Gly Ser
        35                  40                  45

Cys Gly Met Ala Cys Phe Val Pro Gln
    50                  55
```

<210> SEQ ID NO 13
<211> LENGTH: 313
<212> TYPE: PRT
<213> ORGANISM: Artificial Sequence
<220> FEATURE:
<223> OTHER INFORMATION: Synthetic Construct

<400> SEQUENCE: 13

```
Met Lys Asn Thr Ser Ser Leu Cys Leu Leu Leu Val Val Leu Cys
1               5                   10                  15

Ser Leu Thr Cys Asn Ser Gly Gln Ala Ala Gln Glu Pro Gly Lys Gly
            20                  25                  30

Pro Gly Ser Thr Lys Pro Gly Ser Cys Pro Ile Ile Leu Ile Arg Cys
        35                  40                  45

Ala Leu Leu Asn Pro Pro Asn Arg Cys Leu Lys Asp Thr Asp Cys Pro
    50                  55                  60

Gly Ile Lys Lys Cys Cys Glu Gly Ser Cys Gly Val Ala Cys Phe Val
65                  70                  75                  80

Pro Gln Ser Ser Glu Arg Lys Cys Cys Val Glu Cys Pro Pro Cys Pro
            85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
    130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
            165                 170                 175

Gln Asp Trp Leu Asn Gly Lys Glu Tyr Lys Cys Lys Val Ser Asn Lys
        180                 185                 190

Ala Leu Pro Ala Pro Ile Glu Lys Thr Ile Ser Lys Ala Lys Gly Gln
    195                 200                 205

Pro Arg Glu Pro Gln Val Tyr Thr Leu Pro Pro Ser Arg Asp Glu Leu
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
```

```
                245                 250                 255
Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Leu His Glu Ala Leu His Ser His Tyr Thr Gln
    290                 295                 300

Lys Ser Leu Ser Leu Ser Pro Gly Lys
305                 310
```

<210> SEQ ID NO 14
<211> LENGTH: 939
<212> TYPE: DNA
<213> ORGANISM: Artificial Sequence
<220> FEATURE:
<223> OTHER INFORMATION: Synthetic Construct

<400> SEQUENCE: 14

```
atgaaaaata cctcttcttt atgtttgctc ttgttggtgg tgctctgctc tctcacttgt    60
aactctggtc aggctgctca ggaacctgga agggacctg gttctactaa acctggatca   120
tgtccaatta ttcttatcag atgcgctctt ttgaatcctc caaataggtg tttgaaggat   180
acagattgcc ctggtattaa gaaatgttgc gaaggatctt gtggtgttgc ttgctttgtt   240
ccacaatctt cagaaagaaa atgttgcgtt gagtgtcctc catgccctgc tccagagctt   300
ttgggtggac cttctgtttt tcttttttcct ccaaagccaa agatactttt gatgatttct   360
aggactcctg aagttacatg tgttgttgtt gatgtttcac atgaagatcc agaggttaag   420
tttaattggt atgttgatgg agttgaggtt cataatgcta agacaaaacc aagagaagag   480
caatataatt ctacttacag ggttgtttca gttcttacag ttttgcatca ggattggctt   540
aatggtaaag aatacaagtg taaagtttct aataaggctt tgcctgctcc aatcgaaaag   600
actatttcaa aggctaaagg tcaacctaga gagccacagg tttatacact tcctccatct   660
agggatgaat tgactaagaa ccaagtttca cttacatgct tggttaaagg atttaccctt   720
tctgatattg ctgttgaatg ggagtcaaat ggtcagccag agaataacta taagactaca   780
cctccagttc ttgattctga tggttctttc tttctttact ctaagttgac tgttgataag   840
tcaagatggc aacagggtaa tgtttttctct tgctcagttc tccacgaggc actccattca   900
cattcacccc agaagtcact ctctctcagt ccaggaaaa                          939
```

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

```
Ser Ser Glu Arg Lys Cys Cys Val Glu
1               5
```

<210> SEQ ID NO 16
<211> LENGTH: 78
<212> TYPE: DNA
<213> ORGANISM: Artificial Sequence
<220> FEATURE:
<223> OTHER INFORMATION: Synthetic Construct

<400> SEQUENCE: 16

```
ttcaacaatt accaacaaca acaaacaaca aacaacatta caattactat ttacaattac        60
agtcgaaagg aagaagcc                                                     78
```

FUSION PROTEINS FOR TREATING INFLAMMATORY DISEASES

CROSS-REFERENCES TO RELATED APPLICATIONS

The present application is a continuation of International Patent Application No. PCT/US2017/030627, filed May 2, 2017, which claims priority to U.S. Provisional Application No. 62/330,717, filed May 2, 2016, the disclosures of which are herein incorporated by reference in their entirety for all purposes.

REFERENCE TO A SEQUENCE LISTING

The Sequence Listing written in file SequenceListing_070772-222910US-1111910.txt created on Oct. 30, 2018, 21,272 bytes, machine format IBM-PC, MS-Windows operating system, is hereby incorporated by reference in its entirety for all purposes.

BACKGROUND OF THE INVENTION

Lung diseases affect a large population in the United States every year and account for the leading causes of death. Severe alpha-1 antitrypsin deficiency (AATD) is an inherited disorder that may cause lung disease. People with AATD usually develop shortness of breath following mild activity, reduced ability to exercise, and wheezing. Affected individuals often develop emphysema, which is characterized by difficulty in breathing, a hacking cough, and a barrel-shaped chest. Cystic fibrosis (CF) is another genetic disease that affects mostly the lungs, and patients having CF often show difficulty breathing and coughing up mucus as a result of frequent lung infections. Other signs and symptoms include sinus infections, poor growth, fatty stool, clubbing of the fingers and toes, and infertility in males. Both AATD and CF have approximately the same, 1:2500 overall incidence rate in Caucasians.

Currently, the only commercially available intravenous (IV) replacement therapies for humans with AATD or CF are derived from pooled, donated human plasma, and the costs for the infusion products are very high—between $127,000 and $146,000 per year exclusive of infusion costs—and somewhat less for inhalation therapy. Patients with AATD-related emphysema need replacement therapy of 60 mg/kg of weekly alpha-1 antitrypsin (AAT) IV infusions (~200 g/year/patient). These infusion products include Prolastin-C® from Grifols, Aralast NP™ from Baxalta, Zemaira® from CSL Behring and Glassia® from Kamada Ltd via Baxalta. Although these products are safe and effective, the products differ in purity, molecular heterogeneity, and supply is potentially constrained by plasma availability and requires complex and expensive collection, purification, and sterilization and preservation/distribution challenges. Importantly, supply and high costs limit AAT's availability to patients requiring the therapy under present replacement therapy guidelines [4-7]. Plasma-derived AAT is also sensitive to oxidation of methionine at position 358, which causes loss of anti-elastase activity required to be effective in treating AATD [8]. Although recombinant AAT has been produced in E. coli, insect, yeast, mammalian and plant expression systems, the recombinant protein has limited biological activity, low expression, high production cost and/or incorrect glycosylation that can impair both biological activity and pharmacokinetics [9-11].

As such, there is a need in the art for new therapies to treat lung diseases including AATD and CF that overcome the drawbacks associated with current replacement therapies. The present disclosure addresses this and other needs.

BRIEF SUMMARY OF THE INVENTION

In a first aspect, the present disclosure provides a fusion protein comprising a signal peptide, an elafin region, a linker, and a Fc region. In certain embodiments, the elafin region comprises a sequence that is at least 80%, 85%, 90%, 95%, or 98% identical to SEQ ID NO:1. In some embodiments, the fusion protein comprises one or more point mutations in the elafin region relative to SEQ ID NO:1. The point mutations can be one or more of the following mutations in the elafin region of the fusion protein: V5G, V9G, M25L, and M51V. In certain embodiments, the fusion protein comprising the one or more point mutations is more resistant to proteolytic cleavage and/or more resistant to oxidation compared to a control fusion protein without the one or more point mutations in the elafin region.

In certain embodiments, the fusion protein described above comprises a signal peptide comprising a sequence that is at least 80%, 85%, 90%, 95%, or 98% identical to SEQ ID NO:2. The fusion protein can also comprise a linker sequence that is at least 80%, 85%, 90%, 95%, or 98% identical to SEQ ID NOS:3 or 15.

In certain embodiments, the fusion protein described above comprises an Fc region comprising a sequence that is at least 80%, 85%, 90%, 95%, or 98% identical to SEQ ID NO:4. The Fc region of the fusion protein can comprise one or more point mutations, e.g., M203L and/or N209S, in the Fc region as set forth in SEQ ID NO:4. In certain embodiments, the fusion protein has a longer half-life compared to a control fusion protein without the one or more point mutations in the Fc region. In some embodiments, the Fc region of the fusion protein is galactosylated and sialylated, e.g., at an N-glycan site such as at amino acid position 72 of SEQ ID NO:4.

In certain embodiments, the fusion protein comprises a sequence that is at least 80%, 85%, 90%, 95%, or 98% identical to any one of SEQ ID NOS:5-7 and 13.

In another aspect, the present disclosure provides a polynucleotide encoding the fusion protein described above. In certain embodiments, the sequence of the polynucleotide has been codon optimized for expressing the fusion protein in a plant. In certain embodiments, the polynucleotide is at least 80%, 85%, 90%, 95%, or 98% identical to any one of SEQ ID NOS:8-10 and 14.

In another aspect, the present disclosure provides an expression vector comprising the polynucleotide described above. In certain embodiments, the expression vector comprises a CaMV 35S promoter. In certain embodiments, the expression vector comprises an Omega leader sequence of SEQ ID NO:16.

In another aspect, the present disclosure provides a recombinant cell comprising the polynucleotide described above. In certain embodiments, the recombinant cell is a plant cell, e.g., a cell derived from *Nicotiana benthamiana*. In some embodiments, the recombinant cell lacks fucosylation and xylosylation pathways and has galactosylation pathways.

In another aspect, the present disclosure provides a plant comprising the recombinant cell described above. In certain embodiments, the plant is tobacco.

In yet another aspect, the present disclosure provides a method for producing a fusion protein comprising: (a)

providing a polynucleotide described above, (b) introducing the polynucleotide into a plant tissue, thereby expressing the fusion protein in the plant tissue, and (c) recovering the fusion protein from the plant tissue. In certain embodiments, the plant tissue expresses a viral RNA gene silencing suppressor. In certain embodiments, the polynucleotide is introduced into the plant tissue by *Agrobacterium*. In certain embodiments, the polynucleotide is introduced into the plant tissue by vacuum infiltration. In certain embodiments, the introduction of the polynucleotide into the plant is by combining *agrobacterium* with the plant tissue using transient agroinfiltration to form a mixture and to allow infection of at least one plant cell of the plant tissue, and wherein the fusion protein is recovered from the plant tissue after a period of time sufficient for the plant tissue to transiently express the fusion protein, e.g., at least 3 days, at least 4 days, at least 5 days, or at least 6 days.

In yet another aspect, the present disclosure provides a composition comprising the fusion protein described above.

In yet another aspect, the present disclosure provides a method for treating an inflammatory disease in a subject, the method comprising administering to the subject an effective amount of the composition described above. In certain embodiments, the inflammatory disease is selected from the group consisting of an inflammatory pulmonary disease, inflammatory vascular disease, inflammatory systemic disease, and inflammation triggered by reperfusion injury. In certain embodiments, the inflammatory pulmonary disease is selected from the group consisting of alpha-1 antitrypsin deficiency (AATD), cystic fibrosis (CF), and chronic obstructive pulmonary disease (COPD).

Other objects, features, and advantages of the present invention will be apparent to one of skill in the art from the following detailed description and figures.

BRIEF DESCRIPTION OF THE DRAWINGS

FIG. 7C shows an SDS-PAGE analysis of the elafin-Fc fusion protein corresponding to SEQ ID NO:13.

DETAILED DESCRIPTION OF THE INVENTION

I. Introduction

Figure 1:
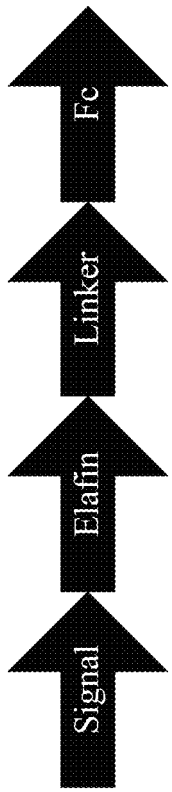
FIG. 1 illustrates the various functional regions of an elafin-Fc fusion protein (corresponding to variant 4 (SEQ ID NO:7)): the signal peptide; the elafin region; the linker; and the Fc region. The elafin region comprises the following point mutations relative to the native elafin: V5G, V9G, M25L, and M51V. The Fc region comprises the following point mutations relative to the native Fc: M203L and N209S.

The present invention provides an elafin-Fc fusion protein for treating inflammatory diseases, especially inflammatory lung diseases, and methods for producing the fusion protein. The fusion protein can be further engineered to be oxidation- and proteolytic-cleavage resistant, as well as having an increased half-life compared to the native human elafin. The fusion protein can also be produced by transient expression in plants, which is rapid (e.g., maximum production of 4-6 days post-agroinfiltration), scalable (e.g., commercial facilities are capable of producing 240 kg/year of purified protein, which is enough to treat 1,200 AATD patients per year), and cost effective. In addition, the plant-produced elafin-Fc fusion protein is oxidation and proteolytic cleavage-resistant, which ensures that the fusion protein has an increased half-life compared to the native human elafin. The addition of IgG Fc at the C-terminus allows efficient and scalable purification of the elafin-Fc fusion protein using standard protein A chromatography. This novel chimeric protein can be produced transiently in a *Nicotiana benthamiana* plant host, providing a scalable, cost-effective approach that enables reductions in both capital investments and cost-of-goods sold (>50%) compared with traditional mammalian cell cultures [73].

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "nucleic acid" or "polynucleotide" includes deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to include a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs include compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" include chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions and/or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and/or alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "fusion protein" commonly refers to a protein that comprises two or more subsequences that are not found in the same relationship to each other in nature. For purposes of this disclosure, the fusion protein refers to the elafin-Fc fusion protein, which comprises a signal peptide, an elafin region, a linker, and a Fc region.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

The term "expression vector" includes a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "therapeutically effective amount" or "effective mount" includes an amount or quantity effective, at dosages and for periods of time necessary, to achieve the desired therapeutic or prophylactic result.

The term "elafin" as used herein encompasses the polypeptide comprising the sequence of SEQ ID NO:1 as well as homologues, derivatives or fragments thereof that have significant sequence identity with SEQ ID NO:1 and retains the inhibitory activity against an elastase, e.g., a human neutrophil elastase or porcine pancreatic elastase.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a fusion protein described herein.

III. Description of the Embodiments

A. Components of the Elafin-Fc Fusion Protein

Native human elafin (SEQ ID NO:1) is a soluble protein with 57 amino acids and a molecular weight of about 6 kDa [17]. Native elafin is expressed predominantly in epithelial tissue and potently inhibits the neutrophil-derived serine proteases (elastase) by a competitive tight-binding mechanism. Native elafin is prone to oxidation at a methionine 25 residue which makes the protein unable to efficiently inhibit elastase activity [15]. In addition, native elafin is cleaved by its cognate enzyme neutrophil elastase in sputum from individuals with cystic fibrosis which will lower the treatment efficacy [16]. Moreover, the half-life of native elafin in plasma is only 115 minutes on average [17].

Figure 2:
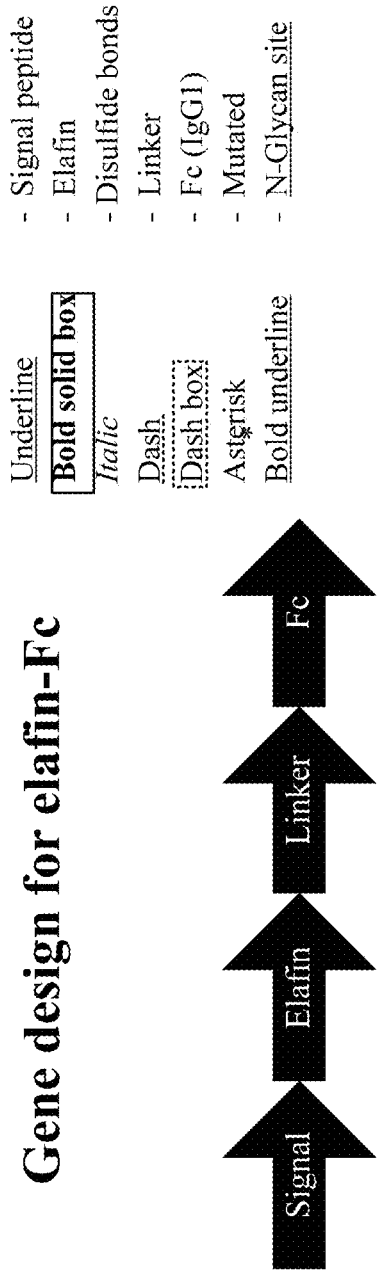
FIG. 2 illustrates the various functional regions of another elafin-Fc fusion protein (corresponding to variant 5 (SEQ ID NO:13)): Variant 5 is identical to variant 4 except for the linker region having a sequence of SEQ ID NO: 15 instead of SEQ ID NO:3.
Figure 3:
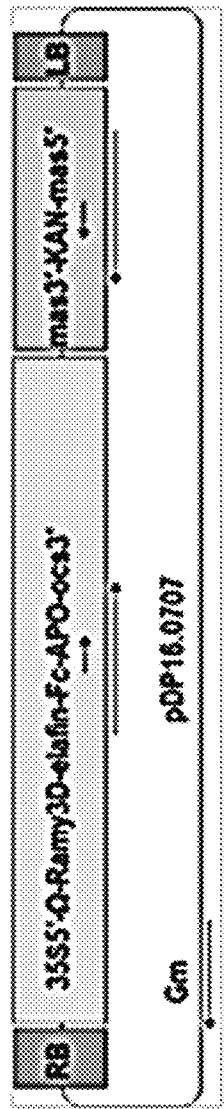
FIG. 3 is a schematic representation of a binary plasmid (pDP16.0707) encoding the elafin-Fc fusion protein corresponding to SEQ ID NO: 13.

The elafin-Fc fusion protein described herein comprises a signal peptide, an elafin region, a linker, and a Fc region. See, e.g., FIGS. 1 and 2. The elafin-Fc fusion protein of the invention comprises an elafin region that may comprise one or more mutations relative to the native elafin. Preferably, the elafin region comprises a sequence that is at least 80%, 85%, 90%, 95%, or 98% identical to the native elafin, SEQ ID NO:1. Generally, any amino acid from the sequence depicted in SEQ ID NO:1 can be deleted and substituted with another amino acid as long as the elafin protein's inhibitory activity on the neutrophil-derived serine proteases, e.g., elastases, is not lost. In some cases, the mutations are introduced via one or more conservative substitutions in order to retain such inhibitory activity.

The elafin region of the fusion protein may comprise mutations that can confer improved properties to the fusion protein, e.g., greater resistance to oxidation and/or greater resistance to proteolytic cleavage as compared to a control fusion protein without the mutations. Mutations that confer greater resistance to proteolytic cleavage to the fusion protein include, for example, the V→G substitution at position 5 ("V5G") of SEQ ID NO:1 or at position 9 ("V9G") of SEQ ID NO: 1 [36]. Mutations that confer increased resistance to oxidation to the fusion protein include, for example, the M→L substitution at position 25 ("M25L") of SEQ ID NO:1 or the M→V substitution at position 51 ("M51V") of SEQ ID NO:1 [40]. The amino acid position 1 is the first amino acid (alanine) in the elafin region (SEQ ID NO: 1). The elafin region of the fusion protein can comprise one or more of these point mutations and the fusion protein can be more resistant to proteolytic cleavage and/or more resistant to oxidation as compared to a control fusion protein without the one or more point mutations.

The signal peptide of the fusion protein can be any signal peptide that can facilitate secretion of the fusion protein from plant cells to the apoplast. In a particular embodiment, the signal peptide is the 25-amino-acid signal peptide from Oryza sativa α-amylase (Ramy3D SP), SEQ ID NO:2. In some embodiments, the signal peptide used in the fusion protein comprises a sequence that is at least 80%, 85%, 90%, 95%, or 98% identical to SEQ ID NO:2.

The linker region of the fusion protein is a polypeptide sequence that connects the elafin region with a Fc region, which provides flexibility for the Fc fusion and allows elafin-Fc to bind the target, e.g., neutrophil elastase [38]. Any immunoglobulin hinge region linker or a portion thereof can be used as the linker for the fusion protein described herein, for example, those described in U.S. Pat. No. 6,165,476. In one embodiment, the linker is the human IgG1 hinge region, which comprises a sequence of SEQ ID NO:3, or a portion thereof. In another embodiment, the linker is the human IgG2 hinge region, which comprises a sequence of SEQ ID NO:15 (see, UniProt Accession No. P01859), or a portion thereof. In some cases, the linker comprises a disulfide bond linkage for Fc dimerization, which can beneficially maintain Fc function. In one embodiment, the linker comprises an amino acid sequence that is at least 80%, 85%, 90%, 95%, or 98% identical to SEQ ID NO:3 or SEQ ID NO:15.

The elafin-Fc fusion protein comprises an immunoglobulin Fc domain ("Fc"). The attachment of the Fc domain to elafin significantly increases the protein's plasma half-life, for at least the following reasons. The Fc domain can interact with the salvage neonatal Fc-receptor, resulting in increased protein stability. The Fc domain also increases the size of the protein, resulting in a slower renal clearance. The Fc domain also folds independently and thus improves the solubility and stability of the elafin protein. The Fc domain additionally offers the technological benefits of easy cost-effective purification by protein-G/A affinity chromatography during manufacture.

In certain embodiments, the Fc region comprises a sequence of SEQ ID NO:4. In some embodiments, the Fc region comprises a sequence that is at least 80%, 85%, 90%, 95%, or 98% identical to SEQ ID NO:4. In some embodiments, the Fc region comprises one or more point mutations that increase the half-life of the fusion protein as compared to the fusion protein without the one or more point mutations in the Fc region. In particular embodiments, the Fc region comprises at least one of the point mutations selected from the group consisting of the M→L substitution at position 203 ("M203L") of SEQ ID NO:4 and the N→S substitution at position 209 ("N209S") of SEQ ID NO:4. In some embodiments, the Fc region of the fusion protein described herein is both galactosylated and sialyated at position 72 of SEQ ID NO:4 to boost the anti-inflammatory effect of the fusion protein [38-39].

Various mutations that can be introduced into the fusion protein and the properties of the protein comprising these mutations are shown in Table 1.

TABLE 1

Various mutations in the elafin-Fc fusion protein and the properties thereof

| Domain | Amino acid position(s) | Mutation(s) | Properties |
| --- | --- | --- | --- |
| Signal peptide (Ramy 3D) | N-terminal | Not mutated | Elafin protein will be targeted to apoplast |
| Elafin | 5 and 9 of SEQ ID NO: 1 | V5G, V9G (GG variant) | Resistant to proteolytic cleavage [36] |
| Elafin | 25 and 51 of SEQ ID NO: 1 | M25L, M51V | Resistant to oxidation (U.S. Pat. No. 5,734,014) |
| Linker | Hinge region of IgG1 Hinge region of IgG2 | Not mutated | Hinge region of IgG1 is more flexible for the Fc fusion which will allow the binding of elafin-Fc to elastase (U.S. Pat. No. 6,165,476; U.S. Pat. Pub. No. 2013/0011399; U.S. Pat. No. 8,980,266) |
| Fc of IgG1 | 203 and 209 of SEQ ID NO: 4 | M203L, N209S | Increased half-life (through FcRn binding) [37]. |
| N-glycan of Fc | 72 of SEQ ID NO: 4 | Expressed in xylose fucose free RNAi and GalT + N. benthamiana | Galactosylation of Fc enhances the anti-inflammatory effect [38]. |
| N-glycan of Fc | 72 of SEQ ID NO: 4 | Sialylation by 1 step in vitro method | Sialylation of Fc also enhances the anti-inflammatory effect [39]. |

As compared to existing products, the elafin-Fc fusion proteins of the present invention have superior properties, as shown in Table 2.

| Feature | Present Invention | FDA approved plasma AAT | Elafin produced from yeast (Proteo Inc.) |
|---|---|---|---|
| Native or recombinant? | Recombinant | Native | Recombinant |
| Source | Plant | Human plasma | Yeast (*Pichia*) |
| Oxidation Resistant? | Yes (Elafin mutant: M25L, M51V) | No (M358) sensitive | No (M25, M51) sensitive |
| Proteolytic cleavage resistant? | Yes (Elafin mutant: V5G, V9G) | No (Pro357-M358) sensitive | No (V5, V9) sensitive |
| Serum half-life? | 21 days (Fc mutant: M203L and N209S) | 5 days | 115 minutes |

B. Sequence Variants

It will readily be appreciated by those of skill in the art that the instant disclosure includes a variety of polynucleotide sequences that are capable of encoding the various functional regions of the elafin-Fc fusion proteins and have the required function. The polynucleotide sequences may encode polypeptides including those sequences with deletions, insertions, or substitutions of different nucleotides, which result in a polynucleotide encoding a polypeptide with at least one functional characteristic of the instant polypeptides, as described herein. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Sequence alterations that do not change the amino acid sequence encoded by the polynucleotide are termed "silent" variations. Due to the degeneracy of the genetic code, with the exception of the codons ATG and TGG, encoding methionine and tryptophan, respectively, any of the possible codons for the same amino acid can be substituted by a variety of techniques, for example, site-directed mutagenesis, available in the art. Accordingly, any and all such variations of a sequence selected from the Sequence Listing are a feature of the instant disclosure.

In addition to silent variations, other conservative variations that alter one or a few amino acids in the encoded elafin-Fc fusion protein, can be made without altering the function of the polypeptide. For example, substitutions, deletions and insertions introduced into the sequences provided herein are also envisioned. Amino acid substitutions are typically of single residues; insertions usually will be on the order of about from 1 to 10 amino acid residues; and deletions will range about from 1 to 30 residues. In particular embodiments, deletions or insertions are made in adjacent pairs, for example, a deletion of two residues or insertion of two residues. Substitutions, deletions, insertions or any combination thereof can be combined to arrive at a sequence. The mutations that are made in the polynucleotide encoding the various functional regions, e.g., the elafin region and the Fc region, of the elafin-Fc fusion protein should not place the sequence out of the reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made when it is desired to maintain the activity of the protein. Various functional regions of the elafin-Fc fusion protein confer specific activities to the fusion protein. For example, the elafin region can confer the activity of inhibiting the neutrophil-derived serine proteases (elastase). Although all conservative amino acid substitutions (e.g., one basic amino acid substituted for another basic amino acid) in a polypeptide will not necessarily result in the polypeptide retaining the same activity as the native polypeptide, it is expected that many of these conservative mutations would result in the polypeptide retaining its activity.

Sequence variants encoding various functional regions of the elafin-Fc fusion proteins can be produced by modifying the respective wild-type sequences according to methods well-known to the skilled in the art. Such methods include, but not limited to, mutagenesis by PCR, which uses primers designed to contain desired changes [41]; nested primers to mutate a target region [42]; and inverse PCR, which amplifies a region of unknown sequence using primers orientated in the reverse direction [43-44]. Many other mutation and evolution methods are also available and expected to be within the skill of a person of ordinary skill in the relevant art.

The polynucleotides encoding the elafin-Fc fusion proteins described herein may also be chemically synthesized in accordance with the desired sequence by a known synthesis process. These sequences can be cloned to an expression vector using well-established cloning procedures.

Chemical or enzymatic alterations of expressed nucleic acids and polypeptides can be performed by standard methods. For example, sequences can be modified by the addition of lipids, sugars, peptides, organic or inorganic compounds, by the inclusion of modified nucleotides or amino acids, or the like. For example, protein modification techniques are illustrated in Ausubel et al. [45]. These modification methods can be used to modify any given sequence, or to modify any sequence produced by the various mutation and artificial evolution modification methods noted herein.

Accordingly, the present invention provides for modification of any given nucleic acid by mutation, chemical or enzymatic modification, or other available methods, as well as for the products produced by practicing such methods, e.g., using the sequences herein as a starting substrate for the various modification approaches.

C. Sequence Identity Determination

Sequence identity or similarity may be determined using standard techniques known in the art, including, but not limited to, the local sequence identity algorithm of Smith & Waterman [46]; the sequence identity alignment algorithm of Needieman & Wunsch [47]; the search for similarity method of Pearson & Lipman [48]; the computerized implementations of these algorithms (GAP, BESTFIT, FASTA, BLAST, Clustal Omega, and TFASTA in the Wisconsin Genetics Software Package, Genetics computer Group, 575 Science Drive, Madison, Wis.); or the Best Fit sequence program described by Devereux et al. [49], preferably using the default settings.

Sequence identity can also be determined by inspection. For example, the sequence identity between sequence A and sequence B, aligned using the software above or manually, can be determined by dividing the length of sequence A, minus the number of gap residues in sequence A, minus the number of gap residues in sequence B, into the sum of the residue matches between sequence A and sequence B, times one hundred.

D. Codon Optimization of the Elafin-Fc Coding Sequence

Generally, codon optimization can be used to increase the rate of translation or to produce recombinant RNA transcripts having desirable properties, such as a longer half-life, as compared with transcripts produced using a non-optimized sequence. Plant and mammals have different codon preferences, so that mammalian genes frequently use codons which are rarely used in plants. As a result, mammalian genes may be expressed very poorly in plants. The present disclosure provides elafin-Fc fusion protein coding sequences that have been engineered to match the codon usage pattern of the plant host to maximize expression efficiency. Methods for codon optimization are readily available, for example, optimizer, accessible free of charge at genomes.urv.es/OPTIMIZER, and GeneGPS® Expression Optimization Technology from DNA 2.0 (Newark, Calif.). In particular embodiments, the coding sequence is codon-optimized for expression in *N. benthamiana* using the OptimumGene™ algorithm from GenScript (Piscataway, N.J.).

E. Vectors and Promoters

The expression vectors provided by this disclosure comprise polynucleotides encoding the elafin-Fc fusion proteins. The expression vectors preferably are plant expression vectors. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a particular aspect of this embodiment, the construct further comprises regulatory sequences, including, for example, a promoter, operably linked to the sequence. Large numbers of suitable vectors and promoters are known to those of skill in the art, and are commercially available.

Typically, the expression vectors include the elafin-Fc coding sequence under the transcriptional control of 5' and 3' regulatory sequences. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Non-limiting examples of constitutive plant promoters which can be useful for expressing the elafin-Fc fusion protein sequence include the cauliflower mosaic virus (CaMV) 35S promoter, which confers constitutive, high-level expression in most plant tissues [50]; the nopaline synthase promoter [51]; the octopine synthase promoter [52]; and the Ramy 3D promoter [64]. A variety of plant gene promoters that regulate gene expression in response to environmental, hormonal, chemical, developmental signals, and in a tissue-active manner can also be used for expression of the elafin-Fc fusion protein.

The expression vectors described herein can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Specific initiation signals can aid in efficient translation of the elafin-Fc coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

F. Host Plants

The expression vector comprising an elafin-Fc fusion protein coding sequence can be introduced into a variety of host plant species, e.g., *Nicotiana benthamiana, Nicotiana tobacum, Lactuca sativa*, and *Solanum lycopersicum*. In particular embodiments, the host plant is *Nicotiana benthamiana*.

In some embodiments, the host plant used for the invention lacks enzymes responsible for plant-specific glycans, such as xylosyltranferases and fucosyltransferases. Genetic knock-out of xylosyltranferases and fucosyltransferases can be established by homologous recombination [53] or by screening mutant libraries [54], or gene silencing [55]. The plant specific glycosylation, i.e., the addition of xylose and fucose, can also be inhibited via the expression of mutant galactosyltransferases, which appear to result in intermediate galactosylated N-glycan structures that are not the substrates for the xylosyl- and fucosyltransferases [56]. In particular embodiments, the host plants lacking enzymes responsible for plant-specific glycans also have human-like glycosylation pathways. Methods for humanizing glycosylation pathways in plants are well known, for example, by introducing into the host plant human β1,4-galactosyltransferases as described in Palacpac et al. [57].

In some embodiments, in order to counteract the host plant's RNA-mediated gene silencing, a defense mechanism that inhibits expression of exogenous protein, a viral RNA silencing suppressor is introduced into the host plant [58]. The presence of the viral RNA silencing suppressor is expected to improve the expression efficiency of the elafin-Fc fusion protein. The viral RNA silencing suppressor gene can be introduced prior to, or simultaneously with, the introduction of elafin-Fc gene into the host plant to boost elafin-Fc protein expression level. Non-limiting examples of RNA gene silencing suppressors that can be used in the invention include P19 and Hc-Pro. In particular embodiments, the viral RNA gene silencing suppressor is Tomato bushy stunt virus P19.

G. *Agrobacterium* Mediated Transformation

The elafin-Fc coding sequence can be transformed into host plants to express the fusion protein, stably or transiently, using methods well established in the art. In particular embodiments, the elafin-Fc coding sequence, under the control of a strong promoter, e.g., the CaMV 35S constitutive promoter, is introduced into a host plant via agroinfiltration and is expressed transiently. Methods of agroinfiltration are well known, for example, as disclosed in Susammenfassung [59].

In some embodiments, the elafin-Fc expression vector is first introduced into the agrobacteria, for example, the EHA105pCH32 strain, using standard methods, such as electroporation or a heat shock method. In certain instances, the transformed agrobacteria are grown in a liquid culture and the resulting bacteria are washed and suspended into a suitable solution to infect the host plant.

A number of ways can be used to infect the host plant. In one embodiment, the bacteria solution is placed in a syringe, and the tip of the syringe is pressed against the underside of a leaf while simultaneously applying gentle counter pressure to the other side of the leaf. The *agrobacterium* is then injected into the airspaces inside the leaf through stomata, or sometimes through a tiny incision made to the underside of the leaf. Vacuum infiltration is another way to penetrate *Agrobacterium* deep into plant tissue. In this procedure, leaf disks, leaves, or whole plants are submerged in a beaker containing the solution, and the beaker is placed in a vacuum chamber. The vacuum is then applied, forcing air out of the stomata. When the vacuum is released, the pressure difference forces solution through the stomata and into the mesophyll. Once inside the leaf the *Agrobacterium* remains in the intercellular space and transfers the elafin-Fc coding sequence in high copy numbers into the plant cells. The gene is then transiently expressed (e.g., no selection for stable integration is performed).

In a specific embodiment of the invention, the transformed agrobacteria are cultured and used to infect 4 to 5-week-old *Nicotiana benthamiana* plants. The leaves of a 4-5 week old *Nicotiana benthamiana* plant are then vacuum infiltrated as described above. Infection takes place either in the presence or absence of a viral RNA gene silencing suppressor. After four days, plant tissue is harvested, homogenized, extracted and tested for amount of protein expression.

H. Protein Expression and Purification

Plant biomass can be harvested and ground and elafin-Fc fusion proteins can be recovered using any suitable extraction buffer. An ultrafiltration can be performed to separate the fusion protein and prepare the extract for protein capturing. Affinity chromatography using Protein A resin is typically performed to purify the elafin-Fc fusion protein.

I. Characterization of the Plant-Made Elafin-Fc Fusion Protein ("PMEF")

Proteolytic Cleavage and Glycosylation

In some embodiments, the purified protein is analyzed for protein purity and coverage using standard techniques such as LC-MS/MS analysis and SDS-PAGE electrophoresis. In addition, site-specific N-glycopeptide analysis using LC-MS/MS can be performed to monitor the glycosylation pattern of the Fc region of the PMEF [28], for example, to confirm that the fusion protein is both galactosylated and sialyated at the N-glycan site (e.g., position 72 of SEQ ID NO:4) in the Fc region to maximize the anti-inflammatory efficacy of the fusion protein [25].

Oxidation

Oxidation of amino acid residues, for example, methionine residues at positions 25 and 51 in the elafin region (SEQ ID NO:1) of the PMEF, can be analyzed in assay mixtures containing physiologically-relevant concentrations of one or more oxidation agents such as $H_2O_2$ and HOCl [29], xenobiotics such as paraquat, CCl4, and acetaminophen, cigarette smoke, reduced transition metals such as Fe21 or Cul, γ-irradiation in the presence of 02, activated neutrophils, ultraviolet (UV) light, ozone, oxidoreductase enzymes, or N-chlorosuccinimide. Methionine residues under these conditions are oxidized to produce methionine sulfoxide, which can be detected by CNBr cleavage/amino acid analysis [60]. Elafin-Fc fusion proteins of the invention containing the mutations selected from the group consisting of M25L and M51V of SEQ ID NO: 1 have less oxidation as compared to a control fusion protein that does not have these mutations.

Half-Life

The half-life of the PMEF can be measured using standard techniques, such as pulse-chase analysis and cycloheximide blocking [61]. The PMEF described herein has a longer half-life as compared to native elafin, e.g., at least 2 fold, 3 fold, 5 fold, or at least 10 fold longer. In some embodiments, the PMEF has a half-life in plasma of at least 1 day, at least 3 days, at least 5 days, at least 7 days, at least 10 days, at least 12 days, at least 15 days, at least 18 days, at least 21 days, or at least 25 days.

Activity in Inhibiting Neutrophilic Elastase

Elafin's inhibitory function on neutrophilic elastase ("NE") can be readily assessed by monitoring the hydrolyzation of a substrate of NE in the presence of PMEF. The hydrolyzation of substrate will be inhibited or stopped in the presence of a PMEF described herein. Many commercial kits are available for testing the inhibitory activity on human neutrophil elastase, for example, the Neutrophil Elastase Inhibitor Screening Kit (ab118971) from Abcam and K782-100 from Biovision.

Alternatively, the NE-inhibitory function of the PMEF can be assessed using sputum expectorated from adult CF patients. CF sputum is an exemplary matrix representing conditions within the inflamed airway since it contains abundant levels of neutrophils that harbor multiple serine proteases that are inhibited by elafin (elastase, proteinase 3, and cathepsin G). CF sputum contains proteins derived from not only neutrophils, but also those secreted by airway epithelial cells, that are the in vivo substrates of neutrophil-derived serine proteases. Thus, this system is more relevant to the human inflammatory airway disease conditions as compared to commercial kits described above. In one particular assay format, spontaneously expectorated sputum from adult CF patients are obtained, divided into aliquots and incubated for various periods of time (0-6 hrs) in the absence or presence of the PMEF. At various intervals, small peptides derived from the activity of endogenous neutrophil proteases are isolated by centrifugation of whole CF sputum through 5 kD molecular weight filters. The isolated peptides are then subjected to LC/MS/MS analysis to determine the sequence, the protein from which the peptides were derived, and quantitative assessment of the proteolytic peptides by previously established methods [30]. This approach using CF sputum thus allows for assessing the efficacy of the PMEF to inhibit neutrophil-derived serine proteases in a complex matrix representative of the inflamed human airway.

J. Targeted Diseases and Evaluating the Efficacy of PMEF Therapy

PMEF can be used to treat inflammatory diseases, e.g., an inflammatory pulmonary disease, inflammatory vascular disease, inflammatory systemic disease, and inflammation triggered by reperfusion injury. In particular embodiments, PMEF can be used to treat an inflammatory pulmonary disease that is selected from the group consisting of alpha-1 antitrypsin deficiency (AATD), cystic fibrosis (CF), and chronic obstructive pulmonary disease (COPD).

AATD is diagnosed by a showing of low serum concentration of alhpha antitrypsin (AAT) and either detection of a functionally deficient AAT protein variant or detection of biallelic pathogenic variants in the gene encoding alpha-1 antitrypsin [62]. AATD patients typically show one or more of the following symptoms: shortness of breath following mild activity, reduced ability to exercise, wheezing, unintentional weight loss, recurring respiratory infections, fatigue, and rapid heartbeat upon standing. The lack of functional AAT resulted from the AATD in these patients often leads to chronic obstructive pulmonary disease (COPD), which include Emphysema, a type of COPD caused by damage to the small air sacs in the lungs. Patients having emphysema often show one or more of the following symptoms: difficulty in breathing, a hacking cough, and a barrel-shaped chest.

CF can be diagnosed with a number of tests. For example, all states screen newborns using a genetic test to detect the presence of faulty cystic fibrosis transmembrane conductance regulator (CFTR). Mutations in CFTR alter the production, structure, or stability of the chloride channel, which impairs the transport of chloride ions and the movement of water into and out of cells. As a result, cells that line the passageways of the lungs, pancreas, and other organs produce mucus that is abnormally thick and sticky. The abnormal mucus obstructs the airways and glands, leading to the characteristic signs and symptoms of cystic fibrosis.

A blood test can also be performed on a newborn to diagnose the presence of CF by showing whether the pancreas is working properly. If a genetic test or blood test suggests CF, a sweat test, which measures the amount of salt in sweat is performed; high salt level confirm a diagnosis of CF. Additional tests such as a chest x-ray, which shows whether the lung is inflamed or scarred, or whether they trap air; a sinus x-ray, which may show signs of sinusitis, a complication of CF; lung function tests, which measure how much air the patient can breathe in and out, how fast the patient can breathe air out, and how well the lung deliver oxygen to the blood. CF patients often show one or more of the following symptoms: difficulty breathing and coughing up mucus as a result of frequent lung infections, sinus infections, poor growth, fatty stool, clubbing of the fingers and toes, and infertility in males.

PMEF therapy is expected to relieve the symptom of the diseases described above by e.g., inhibiting the function of NE, which are present in the respiratory tract secretions of the patients having the diseases described above [3]. Methods for evaluating the efficacy of the PMEF therapy are well known to the medical professionals treating these inflammatory diseases. For example, the clinical benefits for CF or AATD patients receiving PMEF therapy, which correspond to the efficacy of the PMEF, can be measured by one or more of the following criteria: an alleviation of symptoms that are commonly associated with the disease, including, but not limited to the symptoms described above; a decrease in frequencies in lung infections; a reduction in the amount of mucus present in the lungs; a decrease in intestinal blockage, and pulmonary function test results which indicate an improvement in lung function. Non-limiting examples of lung function tests include spirometry, lung volumes test, and diffusion capacity test.

K. Pharmaceutical Compositions Comprising PMEF

The PMEFs of the present invention are useful in the manufacture of a pharmaceutical composition or a medicament for treating inflammatory diseases as described above. Pharmaceutical compositions or medicaments for use in the present invention can be formulated by standard techniques using one or more physiologically acceptable carriers or excipients. Suitable pharmaceutical carriers are described herein and in, e.g., "Remington's Pharmaceutical Sciences" by E. W. Martin. PMEFs of the present invention and their physiologically acceptable salts and solvates can be formulated for administration by any suitable route, including, but not limited to, orally, topically, nasally, rectally, parenterally (e.g., intravenously, subcutaneously, intramuscularly, etc.), and combinations thereof. In some embodiments, the therapeutic agent is dissolved in a liquid, for example, water.

For oral administration, a pharmaceutical composition or a medicament disclosed herein can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titatium dioxide. Tablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

The compounds can be encapsulated in a controlled drug-delivery system such as a pressure controlled delivery capsule [63], a colon targeted delivery system, a osmotic controlled drug delivery system, and the like. The pressure controlled delivery capsule can contain an ethylcellulose membrane. The colon target delivery system can contain a tablet core containing lactulose which is over coated with an acid soluble material, e.g., Eudragit E®, and then overcoated with an enteric material, e.g., Eudragit L®. The osmotic controlled drug delivery system can be a single or more osmotic unit encapsulated with a hard gelatin capsule (e.g., capsule osmotic pump; commercially available from, e.g., Alzet, Cupertino, Calif.). Typically, the osmotic unit contains an osmotic push layer and a drug layer, both surrounded by a semipermeable membrane.

L. Dosage

Pharmaceutical compositions or medicaments can be administered to a subject at a therapeutically effective dose to treat the inflammatory diseases as described herein. In some embodiments, the pharmaceutical composition or medicament is administered to a subject in an amount sufficient to elicit an effective therapeutic response in the subject.

Generally, administered dosages will be effective to deliver picomolar to micromolar concentrations of the active ingredients of the compositions to the appropriate site or sites. However, one of ordinary skill in the art understands that the dose administered will vary depending on a number of factors, including, but not limited to, the subject's body weight, age, individual condition, surface area or volume of the area to be treated, and/or on the form of administration. The size of the dose also will be determined by the existence, nature, and extent of any adverse effects that accompany the administration of a particular compound in a particular subject. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

A unit dosage for oral administration to an individual (e.g., human) of about 50 to 70 kg may contain between about 20 and 300 mg of the active ingredient. Typically, a dosage of the active compounds is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies, and repetition rates.

In some embodiments, the compositions of the invention are administered one or more times a day, e.g., 1, 2, 3, 4, 5, 6, 7, 8, 9, 10, or more times a day.

In some embodiments, the compositions of the invention are administered for about 1 to about 31 days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the compositions of the invention are administered for at least 1 day. In other embodiments, the compositions of the invention are administered for one or more weeks, e.g., 1, 2, 3, 4, 5, 6, 7, 8, 9, 10, 11, 12, 13, 14, or more weeks. In yet other embodiments, the compositions are administered for one or more months, e.g., 1, 2, 3, 4, 5, 6, 7, 8, 9, 10, 11, 12, or more months.

To achieve the desired therapeutic effect, the compositions of the invention may be administered for multiple days at the therapeutically effective daily dose. Thus, therapeutically effective administration of the compositions of the invention to treat a pertinent condition or disease described herein in a subject requires periodic (e.g., daily or twice daily) administration that continues for a period ranging from three days to two weeks or longer. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every day, every other day, or, if higher dose ranges are employed and tolerated by the subject, twice a week.

A dose can be formulated in animal models to achieve a concentration range that includes the $IC_{50}$ (the concentration of the agent that achieves a half-maximal inhibition of symptoms) as determined in cell culture. Such information can be used to more accurately determine useful doses in humans. Levels in stool or an enteric tissue sample can be measured, for example, by high performance liquid chromatography (HPLC). In general, the dose equivalent of the active ingredient of the composition of the invention is from about 1 ng/kg to about 100 mg/kg for a typical subject.

The dosage of a composition of the present invention can be monitored and adjusted throughout treatment, depending on severity of symptoms, frequency of recurrence, and/or the physiological response to the therapeutic regimen. Those of skill in the art commonly engage in such adjustments in therapeutic regimens.

IV. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Methods

1. Cloning

A gene coding for the human elafin followed by a hinge region (human IgG2) and two serines and then the coding sequence of the Fc domain from human IgG1 was codon-optimized for *Nicotiana benthamiana* expression. A nucleotide sequence encoding the Ramy3D signal peptide was fused to the N-terminal of the elafin coding region to enable secretion to the plant apoplast. Also, nucleotides encoding the omega leader sequence were included between the start of the coding region and the CaMV 35S promoter to improve elafin-Fc protein expression. The binary expression vector (pDP16.0707) that was created as a consequence was transformed into *Agrobacterium tumefaciens* EHA105 via electroporation. The expression vector encodes the elafin-Fc fusion protein corresponding to SEQ ID NO:13.

2. Preparation of *Nicotiana benthamiana* Plants

Wild-type *Nicotiana benthamiana* seedlings were grown from seed in soil-filled 4-inch pots in the greenhouse. Two weeks after germination, seedlings were transplanted into 4-inch pots and the soil was supplemented with Osmocote fertilizer (Scotts Miracle-Gro Company, Marysville, Ohio, USA). All of the *Nicotiana benthamiana* plants were grown in the greenhouse with a 16-h photoperiod with the optimal temperature of 30° C. (daytime high) and 18° C. (night time low) for four to six weeks.

3. Bacterial Preparation

Recombinant *Agrobacterium tumefaciens* cells were grown overnight in 10 mL of Luria-Bertani (LB) broth containing appropriate selection antibiotics. For each culture, 2.5 mL was then transferred to 1000 mL flasks containing 250 mL of LB media and grown overnight at 28° C. with 250 rpm shaking. Bacterial cells were harvested by centrifugation at 2600×g for 30 min and resuspended in sterile 10 mM MES buffer (pH 5.6) (Fisher Scientific, Santa Clara, Calif., USA) containing 10 mM MgCl2 and 150 µM acetosyringone (Sigma-Aldrich, St. Louis, Mo., USA). The cell density of the resuspended agrobacterial strains was adjusted to achieve an OD600 of 0.5 for elafin-Fc and p19 strains. These agrobacterial strains were mixed in a 1:1 volume ratio and were incubated in the dark for up to 3 h before infiltration.

4. Agroinfiltration and Plant Incubation

Five-week old potted greenhouse *Nicotiana benthamiana* plants were inverted and immersed in 1000 mL of the agrobacterial solution having 0.02% of Silwet-L-77 (Lehle Seeds, Round Rock, Tex., USA) and placed in a Nalgene container for vacuum infiltration (−25 in Hg) for 2 min before releasing the vacuum. The infiltrated plants were incubated in a controlled environmental growth chamber at 90% humidity and 21° C. for five days, and then the leaves were cut at the petioles and harvested. The agroinfiltrated leaves were stored at −80° C. for further analysis.

5. Harvested Leaves Agroinfiltration and Incubation

For the harvested leaves infiltration approach, leaves were cut at the petioles and harvested leaves were submerged in a 200 mL of agrobacterial solution having 0.02% of Silwet-L-77 (Lehle Seeds, Round Rock, Tex., USA) and placed in a Nalgene container for vacuum infiltration (−25 in Hg) for 2 min before releasing the vacuum. For the incubation, humidity boxes were prepared using Perlite (E.B. Storage) which was soaked in water before using. The storage box was layered with socked Perlite and then metal mesh was placed on the box as a platform for the leaves. Infiltrated leaves were air dried to remove the surface water before incubation in the humidity boxes. Incubation of humidity boxes was performed under dark condition in a controlled environmental growth chamber at 90% humidity and 21° C. for five days, and then the leaves were cut at the petioles and harvested. The agroinfiltrated leaves were stored at −80° C. for further analysis.

6. Extraction

To determine the production level of elafin-Fc protein at five days post-infiltration time point, the biomass was ground in liquid nitrogen at 1:4 ratio (1 g biomass in 4 mL buffer) using phosphate buffered saline (PBS) buffer containing 1 mM EDTA and 2 mM sodium metabisulfite, and incubated for 30 min prior to centrifugation at 2600×g for 30 min. The centrifuged samples were filtered through a 0.22 m filter. Microfiltered plant extract was then used for quantification or purification.

7. Purification

Microfiltered plant extract was purified by Protein-A affinity chromatography (MabSelect SuRe™, GE Healthcare, Marlborough, Mass., USA). 1.5 mL of Protein-A affinity resin was equilibrated with 10 column volumes of PBS buffer followed by sample load at 1 mL/min flow rate. The resin was then washed with 15 to 20 column volumes of PBS buffer. Elution took place by passing 10 column volumes of 100 mM glycine buffer (pH 2.5) to recover the bound elafin-Fc fusion protein. Finally, elution fractions were neutralized with 0.5 M Tris buffer.

8. ELISA Analysis

The production level of elafin-Fc fusion protein in *Nicotiana benthamiana* leaves was quantified using an ELISA method. Microplate wells (Costar 3590, Union City, Calif., USA) were coated with Protein-A of *Staphylococcus aureus* (Southern Biotech, Birmingham, Ala., USA) diluted to 50 µg/mL in PBS Buffer (pH 7.4) and incubated for 1 h at 37° C. Blocking was achieved with 5% non-fat dry milk prepared in PBS buffer using a 15-min incubation. After incubation, plates were washed three times with phosphate buffered saline tween-20 (PBST), samples and controls were diluted in PBS buffer, and 50 µL of each sample was applied directly to the coated wells. A standard curve was generated with 2.3, 6.9, 20.6, 61.7, 185.2, 555.6, 1666.7, and 5000 ng/mL using pure Fc fusion protein (CMG2-Fc protein) (supplied by Planet Biotechnology, Inc., Hayward, Calif., USA) diluted in PBS buffer. Microplates were incubated with 50 µL of diluted samples and standards at 37° C. for 1 h. Then plates were washed three times with PBST buffer and Goat anti-human IgG secondary antibody conjugated with horseradish peroxidase (Southern Biotech) diluted 1:2000 in PBS buffer, which was added. The microplate was incubated for 1 h at 37° C. Detection was performed with 3,3',5,5'-tetramethylbenzidine (TMB) substrate (Promega, Madison, Wis., USA) and the reaction was stopped with 1 N HCl. Finally, the absorbance was measured at 450 nm with a SpectraMax 340C spectrophotometer (Molecular Devices). Each assay was performed in triplicate, and elafin-Fc fusion protein concentrations were interpolated from the linear portion of the standard curve.

9. Dot Blot Analysis

Dot blot analysis was performed by adding different volume of plant extract to a 0.45 µm nitrocellulose membrane (Bio-Rad). Blots were then air dried for 30 min and blocked with 5% non-fat dry milk (NFDM) prepared in PBS buffer for 1 hour at room temperature. The blot was washed 3 times with PBST buffer and incubated with 1:2500 dilution of goat anti-human IgG antibody conjugated with alkaline phosphatase (Southern Biotech) for one hour at room temperature. The blot was washed three times with PBST buffer and developed using AP conjugate substrate kit (Bio-Rad).

10. Immunoblot Analysis

Protein samples were diluted with 4× Laemmli buffer (Bio-Rad, Hercules, Calif., USA) and heated for 5 min at 95° C. with 5% P3-mercaptoethanol (Bio-Rad) for the reducing gel. Electrophoresis was performed for 35 min at 200 V using 4%-20% gradient gel (Bio-Rad). After electrophoresis was completed, the gels were washed three times with DDH2O. Immunoblot analysis was performed by transferring the gel to a 0.45 µm nitrocellulose membrane (Bio-Rad) at 100 V for 90 min. Blots were then washed with PBST buffer and blocked with 5% non-fat dry milk (NFDM) prepared in PBS buffer for overnight at 4° C. The blot was incubated with 1:2500 dilution of goat anti-human IgG antibody conjugated with alkaline phosphatase (Southern Biotech) for one hour at room temperature. The blot was washed three times with PBST buffer and developed using AP conjugate substrate kit (Bio-Rad).

11. SDS-PAGE Analysis

Protein samples were diluted with 4× Laemmli buffer (Bio-Rad, Hercules, Calif., USA) and heated for 5 min at 95° C. with 5% P3-mercaptoethanol (Bio-Rad) for the reducing gel. Electrophoresis was performed for 35 min at 200 V using 4%-20% gradient gel (Bio-Rad). After electrophoresis was completed, the gels were washed three times with DDH2O and stained in Coomassie Brilliant Blue G-250 (Bio-Rad) followed by destaining in DDH2O overnight.

Example 2. Production, Purification, and Characterization of Recombinant Elafin-Fc Fusion Protein (Variant 5)

*Nicotiana benthamiana* plants were transformed with the expression vector encoding SEQ ID NO:13, as described in Example 1. The elafin-Fc fusion protein corresponding to SEQ ID NO:13 comprises a codon-optimized human elafin domain was fused to the Fc domain of human IgG1 using two serines and a hinge region as a fusion protein linker. To secrete the elafin-Fc fusion protein to the *Nicotiana benthamiana* apoplast, the rice α-amylase 3D gene signal peptide (Ramy3D) was included at the N-terminus of the elafin domain. Also, the S2 leader sequence, which is a modified version of the Ω leader sequence from tobacco mosaic virus and corresponds to SEQ ID NO:16, was included to enhance transient protein production. This protein was expressed under the control of Cauliflower mosaic virus (CaMV) 35S promoter. FIG. 7C shows the fusion protein expression from harvested leaf. The produced protein was then purified.

The results show that using the CaMV 35S promoter and co-expression with the Tomato bushy stunt virus p19 gene silencing suppressor, an initial expression level of plant-made elafin-Fc fusion protein of over 300 mg/kg fresh leaf biomass was obtained in just 5 days after vacuum agroinfiltration, which is much higher than the production level of the commercially available yeast expression system for elafin production (10 mg/L culture media) [65].

Downstream bioprocessing of biopharmaceuticals represents some challenge in bioprocess development, and its cost is estimated to range from 65% to 90% of total manufacturing costs depending on the production platform [67]. The Fc domain allows for easy and cost-effective purification by employing Protein A affinity chromatography, a platform technology developed for monoclonal antibody purification. Using this method, under preliminary, non-optimized conditions, we have recovered highly pure plant-made elafin-Fc fusion protein with over 60% recovery, which is higher than that for commercially available yeast-produced, purified elafin (20.3%) [65]. The purity of the plant-made elafin-Fc fusion protein is estimated to be >98% based on SDS-PAGE electrophoresis (FIG. 7). We have optimized the downstream process for plant-made Fc fusion proteins [66].

To determine whether the purification process meets those criteria including identity (amino acid sequence), post-translational modifications (e.g., site-specific glycoforms analysis), activity (inhibition of neutrophil elastase), purity (>98%), host cell protein/DNA and endotoxin, the purity of the plant-made elafin-Fc fusion protein was assessed using SDS-PAGE and Western blot analysis. The integrity and N-glycosylation of the molecule can be assessed using mass spectrometry [66].

Figure 4:
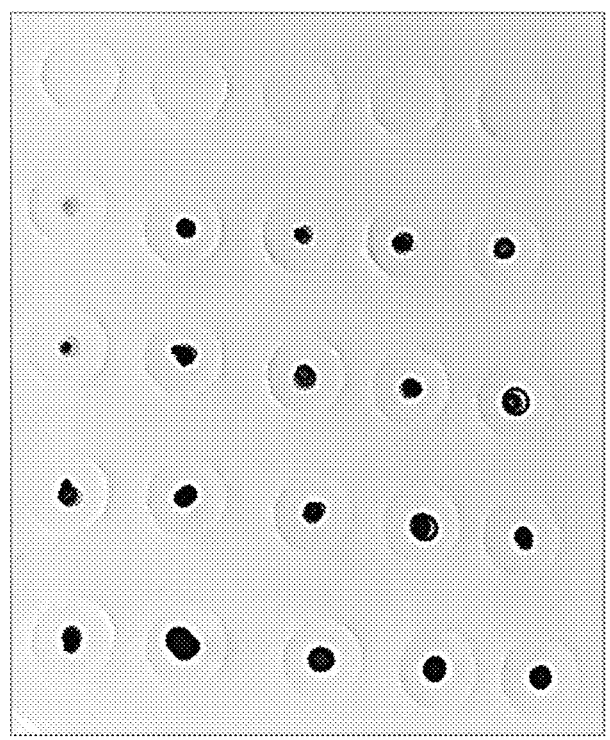
FIG. 4 shows the results of Dot blot experiments performed to detect the elafin-Fc fusion protein corresponding to SEQ ID NO: 13 in plant extracts.
Figure 5A:
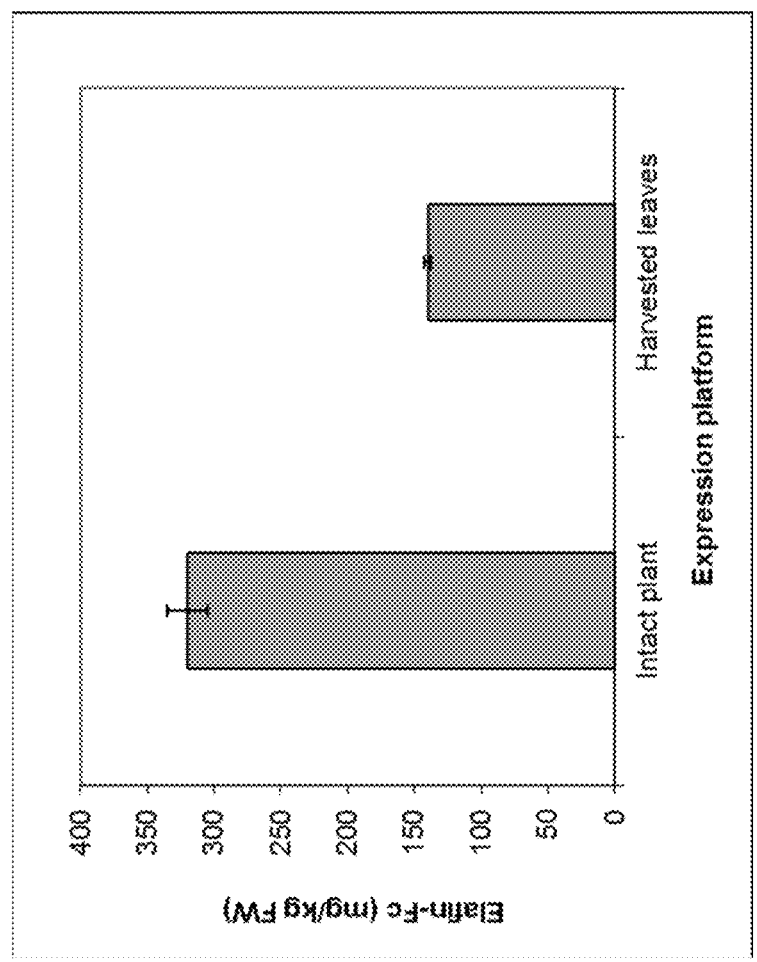
FIG. 5A shows the expression of the elafin-Fc fusion protein corresponding to SEQ ID NO:13 detected by ELISA (FIG. 5A) and Western blot (FIG. 5B). Extracts from intact plant vs. harvested leaves at 5 days of post infiltration were analyzed in ELISA and Western blot. 10 μl of the crude extracts from each sample was analyzed by Western blot.
Figure 5B:
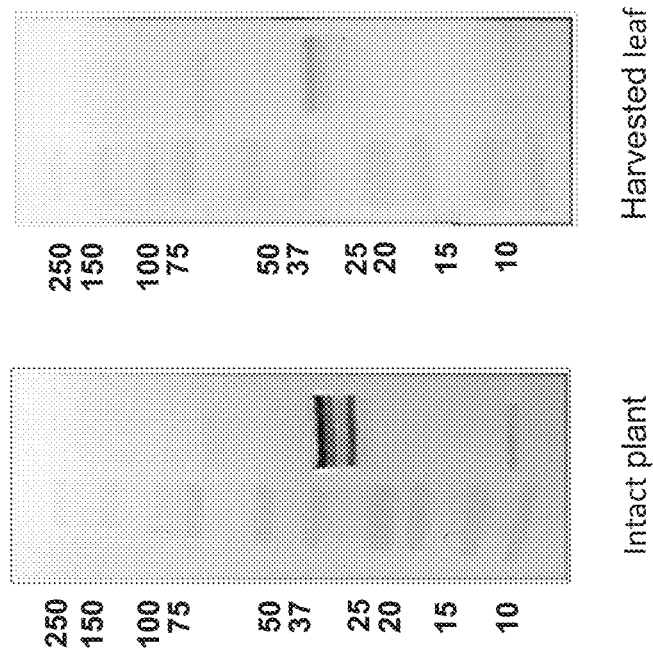
Figure 6A:
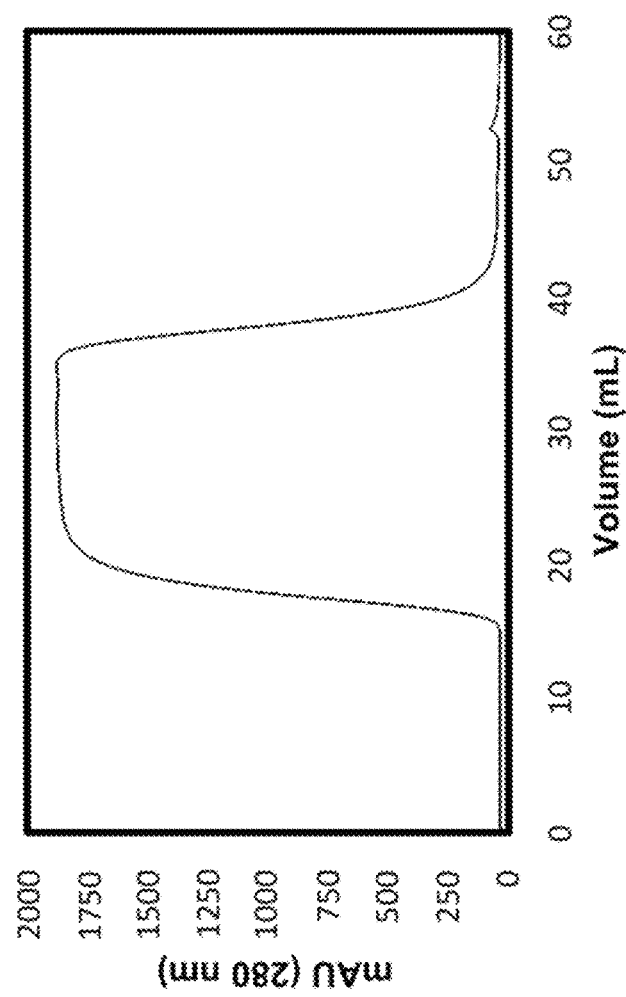
FIG. 6A shows a chromatogram of the proteins extracted from intact plant.
Figure 6B:
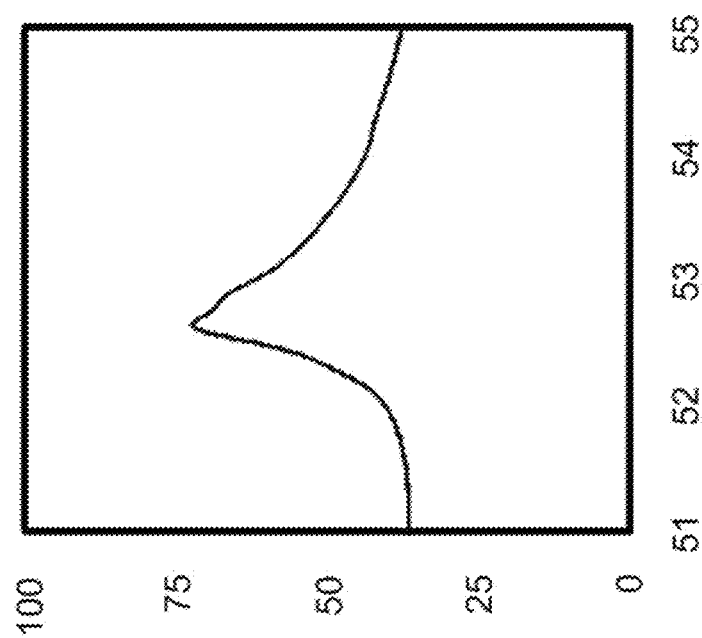
FIG. 6B shows the elution of the elafin-Fc fusion protein corresponding to SEQ ID NO: 13.
Figure 6C:
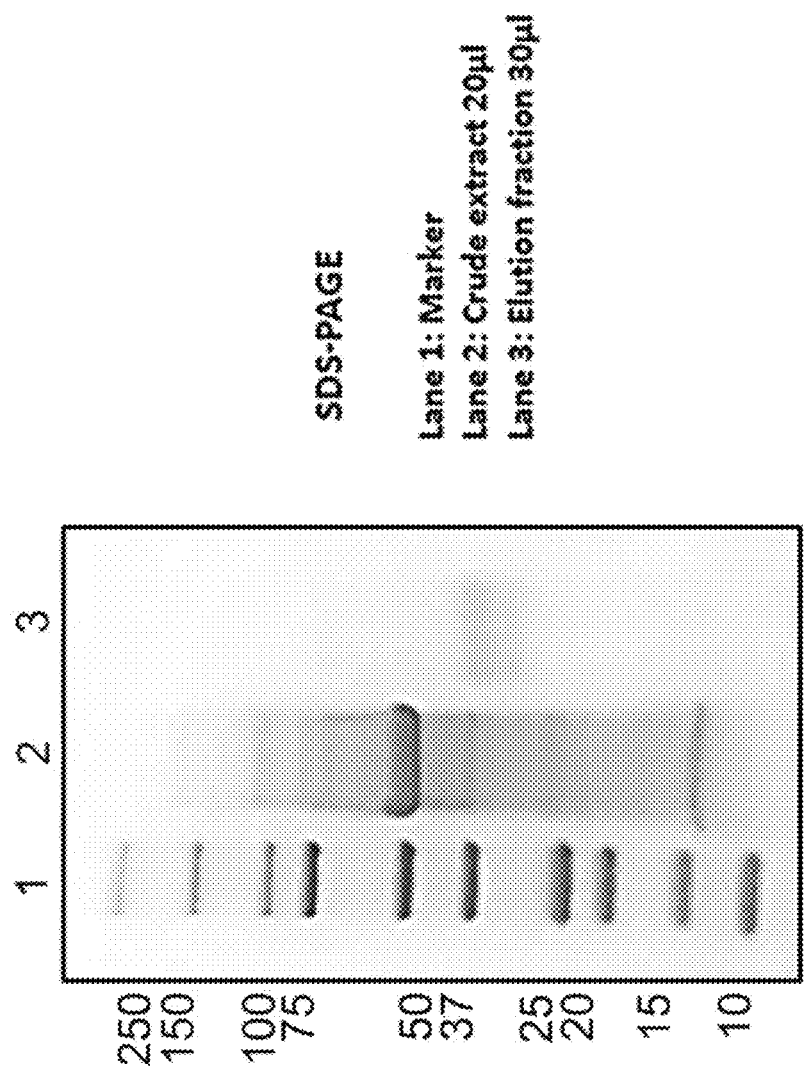
FIG. 6C shows an SDS-PAGE analysis of the elafin-Fc fusion protein corresponding to SEQ ID NO:13.
Figures 7A, 7B:
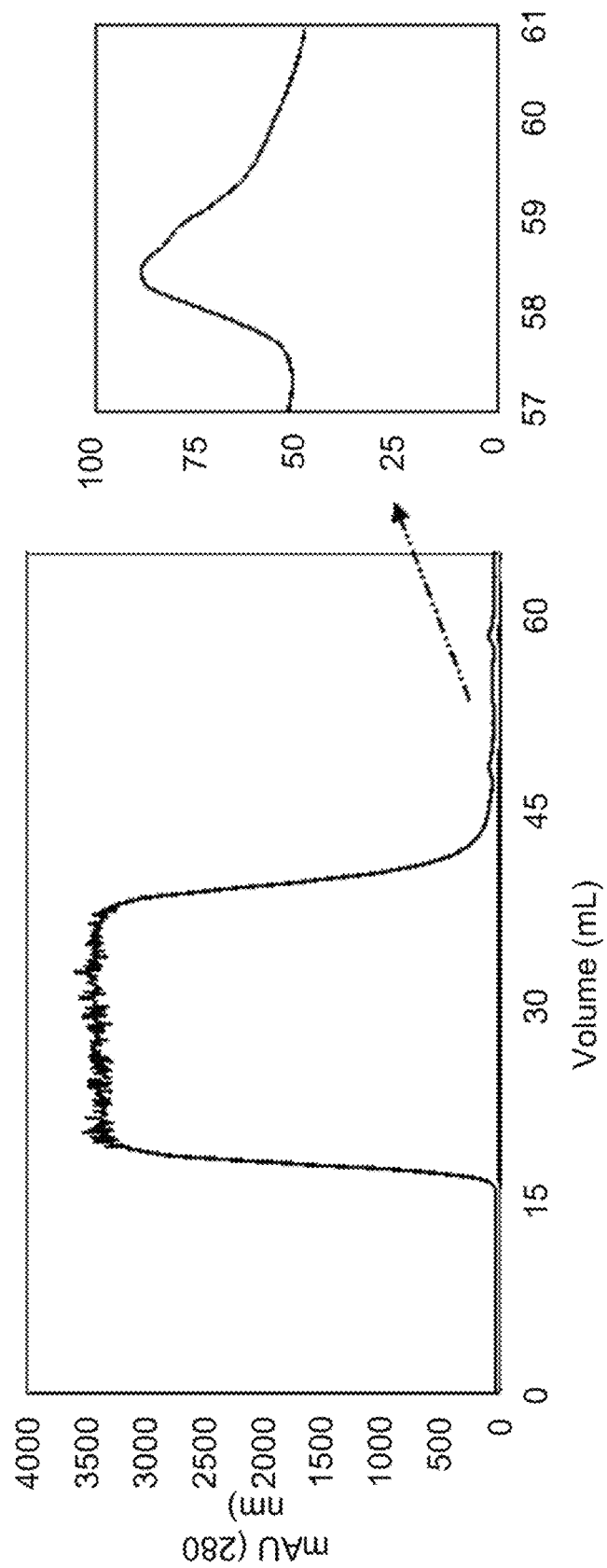
FIG. 7A shows a chromatogram of the proteins extracted from intact plant.
FIG. 7B shows the elution of the elafin-Fc fusion protein corresponding to SEQ ID NO: 13.

The fusion protein was confirmed using Dot-blot experiments performed as described in Example 1 and the results are shown in FIG. 4. The protein production was quantified by ELISA as described in Example 1. The results show that the intact plant produced more than 300 mg/kg of the elafin-Fc fusion protein, while the harvested leaf produced about 150 mg/kg of the elafin-Fc fusion protein (FIG. 5A). The elafin-Fc fusion protein was also detected by Western blots using methods described in Example 1 and the results are shown in FIG. 5B; the left panel shows fusion protein from the intact plant, and the right panel shows the fusion protein from the harvested leaf. To further confirm the production level of the elafin-Fc fusion protein, at the time point that is five days post-infiltration, proteins from intact plant and harvested leaf were extracted, microfiltered, and subjected to protein A affinity chromatography as described above. The elafin-Fc fusion protein was recovered by elution with glycine buffer. The results of the fusion protein from the intact plant are shown in FIG. 6A (chromatogram of the total protein) and FIG. 6B (elution peak of the elafin-Fc fusion protein). The results of the fusion protein from the harvested leaf are shown in FIG. 7A (chromatogram of the total protein) and FIG. 7B (elution peak of the elafin-Fc fusion protein).

Example 3. Production, Purification, and Characterization of Recombinant Elafin-Fc Fusion Protein (Variant 4)

Protein engineering offers a solution for loss of stability and biological activity of therapeutic proteins. Using this approach, researchers were able to design target proteins that were resistant to oxidation and proteolytic cleavage [21,22]. Similarly, many biologically active proteins and peptides have a very short serum half-life due to fast liver and/or renal clearance, which limits their exposure in the target tissue and, consequently, their pharmacological effects. The Fc domain prolongs the serum half-life of Fc-fusion proteins due to pH-dependent binding to the neonatal Fc receptor (FcRn), which salvages the protein from being degraded in endosomes. In addition, from a processing viewpoint, the Fc region allows for an easy cost-effective purification by Protein-G/A affinity chromatography during manufacture [23,24]. However, the limitation of using this expression platform for glycoprotein production is lack of the sialyation pathway. Although native elafin is not glycosylated, the Fc region is glycosylated. Sialyation in the Fc domain was demonstrated to be beneficial in suppression of inflammation using IgG therapy [25]. Thus, engineering the N-glycosylation pathway in plants represents a new production technology platform to address this limitation [26]. This example describes the development of an integrated approach to generate engineered novel elafin-Fc fusion proteins transiently produced via a CaMV 35S expression system in glycoengineered *Nicotiana benthamiana* plants.

In addition, in order to efficiently produce the elafin gene, a mammalian protein, in plants, the elafin gene was codon-optimized for expression in *N. benthamiana* using the codon usage table for this plant from the KEGG database. A codon-optimized elafin-Fc gene, SEQ ID NO:10, was designed for expression in *Nicotiana benthamiana* (GenScript, Piscataway, N.J. 08854, USA). Table 3 shows codon optimization of the elafin gene for expression in *N. benthamiana* or *Pichia pastoris*. In particular, the codon-optimized elafin sequence for expression in *N. benthamiana* is the elafin region of SEQ ID NO:10 and the codon-optimized elafin sequence for expression in *Pichia pastoris* is set forth in SEQ ID NO:11. The codon-optimized elafin-Fc fusion protein gene, e.g., SEQ ID NO:10, can then be synthesized.

TABLE 3

| | Codon Optimization | |
|---|---|---|
| Parameters | Codon optimized elafin gene (*N. benthamiana* expression) | Codon optimized elafin gene (*Pichia* expression system) |
| Codon adaptation index (CAI) | 0.94 | 0.82 |
| Frequency of optimal codons (FOP) | 75% | 57% |
| GC content adjustment (GC) | 42.43 | 39.19 |

Production of Elafin-Fc Fusion Model Protein in Plants

Our goal is to produce elafin-Fc fusion protein with terminal galactosylation by using an apoplast targeting signal peptide. Tobacco is an efficient expression host since it grows fast, has a high biomass density with large porous leaves making it ideal for agroinfiltration. An elafin-Fc fusion protein (SEQ ID NO:7) is produced using a CaMV 35S expression vector by transient expression [27]. The monomeric form of this fusion protein is 34.5 kD and is retained in the endoplasmic reticulum. Elafin-Fc protein production is measured at 4 days post-infiltration in five-week old Nicotiana benthamiana plants. In this approach, a viral RNA gene silencing suppressor (P19) is co-expressed to improve eElafin-Fc fusion protein production.

Purification of Plant-Made Elafin-Fc Fusion Protein (PMEF)

Plant biomass from the elafin-Fc expressing Nicotiana benthamiana plants is ground using liquid nitrogen. 1×PBS buffer is used as the extraction buffer to recover the elafin-Fc protein. A microfiltration step is performed with a 0.22 μm filter followed by ultrafiltration with a 30 kD MWCO filter which is used to prepare the extract for protein capturing. Protein A resin (GE Healthcare) is used for the affinity chromatography step. The purity of the Elafin-Fc fusion protein is expected to be >98% based on SDS-PAGE electrophoresis.

Protein Characterization

The purified elafin-Fc fusion protein is subjected to LC-MS/MS analysis to confirm the protein identity and protein coverage. The results show that 990% coverage of the protein sequence is observed. The site-specific N-glycopeptide analysis of purified elafin-Fc fusion protein is performed according to Nwosu et al [28]. The analysis shows that the elafin-Fc fusion protein having complex type N-glycan with terminal galactosylation and sialylation at amino acid position 72 of SEQ ID NO:4.

Example 4. Assessment of the Safety and Efficacy of Plant-Made Elafin-Fc Fusion Protein (PMEF)

Plant-derived elafin-Fc fusion protein was developed based on three types of mutations: Type 1: mutations engineered on the elafin domain (V5G and V9G) to provide resistance to proteolytic cleavage; Type 2: mutations introduced on the elafin domain (M25L and M51V) to enhance resistance to methionine oxidation; and Type 3: mutations created on the Fc domain (M203L and N209S) increase the serum half-life. Individually, these mutations have been shown not to impact biological activity [36, 37, 68]. To establish the efficacy of plant-derived elafin-Fc fusion protein, in vitro methods can be utilized. Elafin-Fc fusion protein can be compared with commercially available yeast produced recombinant elafin. In brief, to determine stoichiometric inhibition of neutrophil elastase by the elafin-Fc fusion protein, equal concentrations of elafin-Fc can be incubated with neutrophil elastase and changes in fluorescence can be monitored using a neutrophil elastase substrate (N-Methoxy-Succinyl-Pro-Ala-Ala-Val-7-amino-4-methyl-coumarin) [69]. To determine proteolytic cleavage resistance of elafin-Fc fusion protein, Pseudomonas protease and neutrophil elastase can be incubated with elafin-Fc fusion protein and resistance assessed at various incubation time point using Western blot and mass spectrometry analysis [70]. To determine oxidation resistance of elafin-Fc fusion protein, different concentrations of $H_2O_2$ can be incubated with elafin-Fc fusion protein and resistance assessed using a neutrophil elastase inhibition assay and mass spectrometry [71]. To determine the increased serum half-life of the elafin-Fc fusion protein, neonatal Fc receptor binding efficacy of elafin-Fc fusion protein can be estimated using an ELISA method [72]. The plant-made elafin-Fc fusion protein described herein is oxidant-resistant, has a long circulatory half-life, and is a cost-effective and safe therapy for lung disease, providing a homogeneous and expandable supply of therapeutics for inflammatory lung disease at a lower cost.

Any potential therapeutic agent requires basic in vitro cellular and animal toxicity profiles in the early stages of development. This example further describes performing cell incubation studies of the recombinant elafin-Fc fusion protein variants with human bronchial epithelial (HBE) cells. These cells can be used for our initial toxicology studies. In order to examine safety aspects, the toxicological profiles of elafin-Fc fusion protein can be studied using HBE cells in a dose and time dependent manner. In addition, the biological response of HBE cells can be assessed when exposed to elafin-Fc fusion protein using proteomic approaches. From an efficacy standpoint, inhibition kinetics of elastase can be tested under normal and oxidant exposed elafin-Fc fusion protein when incubated with the HBE cell line.

(i) Assessing the Resistance of Elafin-Fc Fusion Protein to Inactivation by Inflammatory Oxidants Hydrogen Peroxide and Hypochlorous Acid Residual human neutrophil elastase (HNE) or porcine pancreatic elastase (PPE) activity assays can be performed to determine the efficacy of elafin-Fc variants in inhibiting elastase. Yeast recombinant elafin and commercial available AAT can be used as controls for this assay. Oxidation resistance can be determined for the plant-made elafin-Fc fusion variants and the control while incubating them in a assay buffer containing physiologically relevant concentrations of $H_2O_2$ and HOCl [29].

(ii) Assessing the Ex Vivo Efficacy of Elafin-Fc Variants to Inhibit Neutrophil-Derived Serine Proteases in Sputum from CF Patients Using "Peptidomics" Mass Spectrometry.

In order to expand the assessment of elafin-Fc fusion protein efficacy to more complicated systems directly relevant to inflammatory airway disease conditions, sputum expectorated from adult CF patients can be used. CF sputum is an exemplary matrix representing conditions within the inflamed airway since it contains abundant levels of neutrophils that harbor multiple serine proteases that are inhibited by elafin (e.g., elastase, proteinase 3, and cathepsin G). CF sputum contains proteins derived from not only neutrophils, but also those secreted by airway epithelial cells, that are the in vivo substrates of neutrophil-derived serine proteases. Spontaneously expectorated sputum from adult CF patients can be obtained, divided into aliquots and incubated for various periods of time (0-6 hrs) in the absence or presence of elafin-Fc variants. At various intervals, small peptides derived from the activity of endogenous neutrophil proteases can be isolated by centrifugation of whole CF sputum through 5 kD molecular weight filters. The isolated peptides can then be subjected to LC/MS/MS analysis to determine the sequence, the protein from which the peptides were derived, and quantitative assessment of the proteolytic peptides by previously established methods [30]. This approach using CF sputum allows for assessing the efficacy of elafin-Fc fusion protein to inhibit neutrophil-derived serine proteases in a complex matrix representative of the inflamed human airway, and establish a procedure for defining the inflamed airway 'peptidome'. In addition, the approach has added value in that it can elucidate novel 'biomarkers' of inflammatory airway diseases.

Example 5. Development of a Novel Therapy for Lung Disease Using a Mouse Model

Chronic obstructive pulmonary disease (COPD), manifested as emphysema and chronic airway obstruction, can be exacerbated by bacterial and viral infections. Although the frequency of exacerbations increases as the disease progresses, the mechanisms underlying this phenomenon are largely unknown, and there is a need for a simple in vivo exacerbation model. Mice exposed to tobacco smoke may represent a novel model of tobacco smoke-induced lung inflammation and disease. However, this approach is not only time consuming but also costly. Thus, in this study, a simple in vivo exacerbation model of COPD can be established by a single administration of elastase followed by lipopolysaccharide (LPS). This simple mouse model mimics human cases and can be useful for elucidating its mechanism and developing therapeutic strategies. In this example, plant-made elafin-Fc fusion proteins can be tested on an elastase and LPS exposed mice model. An exemplary experimental protocol is as follows: Mice aged 10 to 14 weeks are anesthetized by intraperitoneal injection of 1.25% (wt/vol) tribromoethanol, followed by spraying of 4.2 U of porcine pancreatic elastase (PPE) dissolved in 100 ml of sterile PBS or 100 ml of PBS alone (control animals) into the trachea using a MicroSprayer drug delivery device. After 21 days, mice are given intratracheal administration of LPS (1 mg/kg) dissolved in 100 ml of sterile PBS into the trachea of the control and PPE-exposed mice [31-34]. Efficacy of plant made elafin-Fc fusion protein variants can be compared with commercially available yeast-derived elafin protein in terms of serum circulatory half-life, oxidation resistance and proteolytic cleavage resistance. In order to find an optimal drug administration route, the mouse model can be treated by either inhalation or intraperitoneal injection (IP) with elafin-Fc fusion protein variants and controls.

Example 6. Treating a Human Patient with Lung Disease Using PMEF

A female patient has been diagnosed with CF since birth. She has difficulty breathing and often coughs up mucus. She has a history of frequent lung infections, sinus infections, poor growth, fatty stool and she appears to have clubbing of the fingers and toes.

Her physician prescribes and she is given an intravenous infusion of PMEF with an optimal dose once a week, e.g., using a dosing regimen based on drug efficacy. After a period of four months, the lung inflammation symptoms are lessened, less mucus is present in her lungs and her pulmonary function has improved. She also reports less frequent lung infections.

V. References

1. Sheludko Y V (2008) *Agrobacterium*-mediated transient expression as an approach to production of recombinant proteins in plants. Recent Pat Biotechnol 2: 198-208.
2. Shamloul M, Trusa J, Mett V, Yusibov V (2014) Optimization and utilization of *Agrobacterium*-mediated transient protein production in *Nicotiana*. J Vis Exp.
3. Griese M, Latzin P, Kappler M, Weckerle K, Heinzlmaier T, et al. (2007) alpha1-Antitrypsin inhalation reduces airway inflammation in cystic fibrosis patients. Eur Respir J 29: 240-250.
4. Society A T (2003) American Thoracic Society/European Respiratory Society statement: standards for the diagnosis and management of individuals with alpha-1 antitrypsin deficiency. Am J Respir Crit Care Med 168: 818-900.
5. Tonelli A R, Brantly M L (2010) Augmentation therapy in alpha-1 antitrypsin deficiency: advances and controversies. Ther Adv Respir Dis 4: 289-312.
6. Stoller J K, Aboussouan L S (2012) A review of alphal-antitrypsin deficiency. Am J Respir Crit Care Med 185: 246-259.
7. Kumpalume P, Podmore A, LePage C, Dalton J (2007) New process for the manufacture of alpha-1 antitrypsin. J Chromatogr A 1148: 31-37.
8. Taggart C, Cervantes-Laurean D, Kim G, McElvaney N G, Wehr N, et al. (2000) Oxidation of either methionine 351 or methionine 358 in alpha 1-antitrypsin causes loss of anti-neutrophil elastase activity. J Biol Chem 275: 27258-27265.
9. Bischoff R, Speck D, Lepage P, Delatre L, Ledoux C, et al. (1991) Purification and biochemical characterization of recombinant alpha 1-antitrypsin variants expressed in *Escherichia coli*. Biochemistry 30: 3464-3472.
10. Arjmand S, Bidram E, Lotfi A S, Shamsara M, Mowla S J (2011) Expression and Purification of Functionally Active Recombinant Human Alpha 1-Antitrypsin in Methylotrophic Yeast *Pichia pastoris*. Avicenna J Med Biotechnol 3: 127-134.
11. Agarwal S, Singh R, Sanyal I, Amla D V (2008) Expression of modified gene encoding functional human alpha-1-antitrypsin protein in transgenic tomato plants. Transgenic Res 17: 881-896.
12. Shaw L, Wiedow O (2011) Therapeutic potential of human elafin. Biochem Soc Trans 39: 1450-1454.
13. Simpson A J, Wallace W A, Marsden M E, Govan J R, Porteous D J, et al. (2001) Adenoviral augmentation of elafin protects the lung against acute injury mediated by activated neutrophils and bacterial infection. J Immunol 167: 1778-1786.
14. Proteo I (2013) FDA Grants Orphan Drug Designation to Elafin for Prevention of Inflammatory Complications of Transthoracic Esophagectomy.
15. Nobar S M, Zani M L, Boudier C, Moreau T, Bieth J G (2005) Oxidized elafin and trappin poorly inhibit the elastolytic activity of neutrophil elastase and proteinase 3. FEBS J 272: 5883-5893.
16. Guyot N, Butler M W, McNally P, Weldon S, Greene C M, et al. (2008) Elafin, an elastase-specific inhibitor, is cleaved by its cognate enzyme neutrophil elastase in sputum from individuals with cystic fibrosis. J Biol Chem 283: 32377-32385.
17. Wiedow O, Bargmann B, Kahlke B, Shaw L, Wichmann N (2011) Novel uses of elafin. Google Patents.
18. Medi-Span Price Rx, wolterskluwercdi.com/price-rx/.
19. Lucas S D, Costa E, Guedes R C, Moreira R (2013) Targeting COPD: advances on low-molecular-weight inhibitors of human neutrophil elastase. Med Res Rev 33 Suppl 1: E73-101.
20. Huang W, Giddens J, Fan S Q, Toonstra C, Wang L X (2012) Chemoenzymatic glycoengineering of intact IgG antibodies for gain of functions. J Am Chem Soc 134: 12308-12318.
21. Griffiths S W, Cooney C L (2002) Relationship between Protein Structure and Methionine Oxidation in Recombinant Human α1-Antitrypsin. Biochemistry 41: 6245-6252.
22. Lauer G, Sollberg S, Cole M, Krieg T, Eming S A (2002) Generation of a novel proteolysis resistant vascular endothelial growth factor165 variant by a site-directed mutation at the plasmin sensitive cleavage site. FEBS Letters 531: 309-313.
23. Czajkowsky D M, Hu J, Shao Z, Pleass R J (2012) Fc-fusion proteins: new developments and future perspectives. EMBO Mol Med 4: 1015-1028.

24. Beck A, Reichert J M (2011) Therapeutic Fc-fusion proteins and peptides as successful alternatives to antibodies. MAbs 3: 415-416.
25. Anthony R M, Kobayashi T, Wermeling F, Ravetch J V (2011) Intravenous gammaglobulin suppresses inflammation through a novel T(H)2 pathway. Nature 475: 110-113.
26. Castilho A, Strasser R, Stadlmann J, Grass J, Jez J, et al. (2010) In planta protein sialylation through overexpression of the respective mammalian pathway. J Biol Chem 285: 15923-15930.
27. Arzola L, Chen J, Rattanaporn K, Maclean J M, McDonald K A (2011) Transient co-expression of post-transcriptional gene silencing suppressors for increased in planta expression of a recombinant anthrax receptor fusion protein. Int J Mol Sci 12: 4975-4990.
28. Strum J S, Nwosu C C, Hua S, Kronewitter S R, Seipert R R, et al. (2013) Automated Assignments of N- and O-Site Specific Glycosylation with Extensive Glycan Heterogeneity of Glycoprotein Mixtures. Analytical Chemistry 85: 5666-5675.
29. Nowak D, Ruta U (1990) Nicotine inhibits alpha-1-proteinase inhibitor inactivation by oxidants derived from human polymorphonuclear leukocytes. Experimental Pathology 38: 249-255.
30. Kultz D, Li J, Gardell A, Sacchi R (2013) Quantitative molecular phenotyping of gill remodeling in a cichlid fish responding to salinity stress. Mol Cell Proteomics 12: 3962-3975.
31. Schmelzer K R, Kubala L, Newman J W, Kim I H, Eiserich J P, et al. (2005) Soluble epoxide hydrolase is a therapeutic target for acute inflammation. Proc Natl Acad Sci USA 102: 9772-9777.
32. Corbacho A M, Eiserich J P, Zuniga L A, Valacchi G, Villablanca A C (2007) Compromised aortic vasoreactivity in male estrogen receptor-alpha-deficient mice during acute lipopolysaccharide-induced inflammation. Endocrinology 148: 1403-1411.
33. Kobayashi S, Fujinawa R, Ota F, Kobayashi S, Angata T, et al. (2013) A single dose of lipopolysaccharide into mice with emphysema mimics human chronic obstructive pulmonary disease exacerbation as assessed by microcomputed tomography. Am J Respir Cell Mol Biol 49: 971-977.
34. Silvie Kremserova T P, Karel Soucek, Anna Klinke, Stephan Baldus, Jason P. Eiserich, and Lukas Kubala (2016) Lung neutrophilia in myeloperoxidase deficient mice during the course of acute pulmonary inflammation. Oxidative Medicine and Cellular Longevity. Article I D 5219056, accepted January 2016.
35. Wang L, Yang J, Guo L, Uyeminami D, Dong H, et al. (2012) Use of a soluble epoxide hydrolase inhibitor in smoke-induced chronic obstructive pulmonary disease. Am J Respir Cell Mol Biol 46: 614-622.
36. Small et al. (2015) A functional variant of elafin with improved anti-inflammatory activity for pulmonary inflammation. Molecular therapy 23 (1): 24-31.
37. Zalevsky et al (2010) Nature Biotechnology 28 (2): 157-159.
38. Karsten et al. (2012) Anti-inflammatory activity of IgG1 mediated by Fc galactosylation and association of FcγRIIB and dectin-1. Nature Medicine, 18 (9): 1401-6.
39. Kaneko et al. (2006) Anti-Inflammatory Activity of Immunoglobulin G Resulting from Fc Sialylation. Science Report 313 (5787): 670-673.
40. U.S. Pat. No. 5,734,014.
41. Zoller M J (1991) New molecular biology methods for protein engineering. Curr. Opin. Biotechnol. 2(4): 526-531.
42. Ho S N, Hunt H D, et al. (1989) Site-directed mutagenesis by overlap extension using the polymerase chain reaction. Gene, 77(1): 51-59.
43. Ochman H, Gerber A S, et al. (1988) Genetic applications of an inverse polymerase chain reaction. Genetics, 120(3): 621-623;
44. Hemsley A, Arnheim N, et al. (1989) A simple method for site-directed mutagenesis using the polymerase chain reaction. Nucleic Acids Res, 17(16): 6545-6551.
45. Ausubel et al. Current Protocols in Molecular Biology, Current Protocols, a joint venture between Greene Publishing Associates, Inc. and John Wiley & Sons, Inc., (supplemented through 2007).
46. Smith & Waterman (1981) Comparison of biosequences. Adv. Appl. Math. 2: 482-489.
47. Neediemann & Wunsch (1970) A general method applicable to the search for similarities in the amino acid sequence of two proteins. J. MoL, Biol. 48:443-453.
48. Pearson & Lipman (1988) Improved tools for biological sequence comparison. Proc. Natl. Acad. Sci. USA 85: 2444-2448.
49. Devereux et al. (1984) Identification of DNA sequences required for activity of the cauliflower mosaic virus 35S promoter. Nucl. Acid Res. 12: 387-395.
50. Odel et al. (1985) Identification of DNA sequences required for activity of the cauliflower mosaic virus 35S promoter. Nature 313:810-812.
51. An et al. (1988) Organ-Specific and Developmental regulation of thenopaline synthase promoter in transgenic tobacco plants. Plant Physiol. 88:547-552.
52. Fromm et al. (1989) An octopine synthase enhancer element directs tissue-specific expression and binds ASF-1, a factor from tobacco nuclear extracts. Plant Cell 1: 977-984.
53. Huether C M, Lienhart O, Baur A et al. (2005) Glyco-engineering of moss lacking plant-specific sugar residues. Plant Biol. (Stuttg.) 7(3): 292-299.
54. Schahs et al. (2007) Production of a monoclonal antibody in plants with a humanized N-glycosylation pattern. Plant Biotechnol. J. 5(5): 657-663.
55. Strasser R, Stadlmann J, Schahs M et al. (2008) Generation of glyco-engineered *Nicotiana benthamiana* for the production of monoclonal antibodies with a homogeneous human-like N-glycan structure. Plant Biotechnol. J. 6(4) 392-402.
56. Bakker H, Rouwendal G J, Karnoup A S et al. (2006) An antibody produced in tobacco expressing a hybrid β 1,4-galactosyltransferase is essentially devoid of plant carbohydrate epitopes. Proc. Natl. Acad. Sci. USA 103 (20):7577-7582.
57. Palacpac N Q, Yoshida S, Sakai H et al. (1999) Stable expression of human b1,4-galactosyltransferase in plant cells modifies N-linked glycosylation patterns. Proc. Natl Acad. Sci. USA 96(8): 4692-4697.
58. viralzone.expasy.org/all_by protein/891.html.
59. U.S. Pat. No. 8,674,178.
60. K. L. Maier, A. G. Lenz, I. Beck-Speier, and U. Costabel (1995) Analysis of methionine sulfoxide in proteins, Methods Enzymol., 251, 455-461.
61. Zhou (2004) Determining protein half-lives Methods Mol. Biol. 284: 67-77.
62. James K. Stoller et al., (2014) GeneReviews [internet], available at ncbi.nlm.nih.gov/books/NBK1519/.

63. Takaya et al. (1998) Importance of dissolution process on systemic availability of drugs delivered by colon delivery system. *J. Control Rel.,* 50:111-122.
64. Mitsunaga et al., (1994) Sequence-specific interactions of a nuclear protein factor with the promoter region of a rice gene for α-amylase, RAmy3D. Nucleic Acids Research, 11: 1948-1952.
65. Bourbonnais Y, Larouche C, Tremblay G M (2000) Production of full-length human pre-elafin, an elastase specific inhibitor, from yeast requires the absence of a functional yapsin 1 (Ypslp) endoprotease. Protein Expr Purif 20: 485-491.
66. Karuppanan K, Duhra-Gill S, Kailemia M J, Phu M L, Lebrilla C B, et al. (2017) Expression, Purification, and Biophysical Characterization of a Secreted Anthrax Decoy Fusion Protein in *Nicotiana benthamiana*. Int J Mol Sci 18.
67. Wilken L R, Nikolov Z L (2012) Recovery and purification of plant-made recombinant proteins. Biotechnol Adv 30: 419-433.
68. Yoshiaki Ishima N O, Masaya Yoshida, Sakae Amagaya, Akira Kaji (1998) Elafin derivative.
69. Weldon S, McNally P, McElvaney N G, Elbom J S, McAuley D F, et al. (2009) Decreased levels of secretory leucoprotease inhibitor in the *Pseudomonas*-infected cystic fibrosis lung are due to neutrophil elastase degradation. J Immunol 183: 8148-8156.
70. Guyot N, Bergsson G, Butler M W, Greene C M, Weldon S, et al. (2010) Functional study of elafin cleaved by *Pseudomonas aeruginosa* metalloproteinases. Biol Chem 391: 705-716.
71. Silberstein D Z, Karuppanan, K., Cross, C., Eiserich, J. & McDonald, K. (2016) Plant based production, purification and characterization of oxidation resistant alpha-1 antitrypsin. In: Davies K J, editor. SfRBM's 23 Annual meeting Los Angeles, Calif., USA: Free radical biology & medicne pp. S50.
72. Grevys A, Bern M, Foss S, Bratlie D B, Moen A, et al. (2015) Fc Engineering of Human IgG1 for Altered Binding to the Neonatal Fc Receptor Affects Fc Effector Functions. J Immunol 194: 5497-5508.73. Nandi S, Kwong A T, Holtz B R, Erwin R L, Marcel S, et al. (2016) Techno-economic analysis of a transient plant-based platform for monoclonal antibody production. mAbs: 00-00.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims. In addition, each reference provided herein is incorporated by reference in its entirety to the same extent as if each reference was individually incorporated by reference. Where a conflict exists between the instant application and a reference provided herein, the instant application shall dominate.

VI. Exemplary Embodiments

Exemplary embodiments provided in accordance with the presently disclosed subject matter include, but are not limited to, the claims and the following embodiments:

1. A fusion protein comprising a signal peptide, an elafin region, a linker, and a Fc region.
2. The fusion protein of embodiment 1, wherein the elafin region comprises a sequence that is at least 80%, 85%, 90%, 95%, or 98% identical to SEQ ID NO:1.
3. The fusion protein of embodiment 1 or 2, wherein the fusion protein comprises one or more point mutations in the elafin region relative to SEQ ID NO: 1.
4 The fusion protein of embodiment 3, wherein the fusion protein is more resistant to proteolytic cleavage and/or oxidation compared to a control fusion protein without the one or more point mutations in the elafin region.
5. The fusion protein of embodiment 3 or 4, wherein fusion protein comprises one or more of the following point mutations in the elafin region: V5G, V9G, M25L, and M51V.
6. The fusion protein of embodiment 5, wherein the fusion protein comprises the V5G, V9G, M25L, and M51V point mutations in the elafin region.
7. The fusion protein of any one of the embodiments 1 to 6, wherein the signal peptide comprises a sequence that is at least 80%, 85%, 90%, 95%, or 98% identical to SEQ ID NO:2.
8. The fusion protein of any one of the embodiments 1 to 7, wherein the linker comprises a sequence that is at least 80%, 85%, 90%, 95%, or 98% identical to SEQ ID NO:3 or SEQ ID NO:15.
9. The fusion protein of any one of the embodiments 1 to 8, wherein the Fc region comprises a sequence that is at least 80%, 85%, 90%, 95%, or 98% identical to SEQ ID NO:4.
10. The fusion protein of embodiment 9, wherein the fusion protein comprises one or more point mutations in the Fc region relative to SEQ ID NO:4.
11. The fusion protein of embodiment 10, wherein the fusion protein has a longer half-life compared to a control fusion protein without the one or more point mutations in the Fc region.
12. The fusion protein of embodiment 10 or 11, wherein the fusion protein comprises one or more of the following point mutations in the Fc region: M203L and N209S.
13. The fusion protein of embodiment 12, wherein the fusion protein comprises the M203L and N209S point mutations in the Fc region.
14. The fusion protein of embodiment 1, wherein the fusion protein comprises a sequence that is at least 80%, 85%, 90%, 95%, or 98% identical to any one of SEQ ID NOS:5-7 and 13.
15. The fusion protein of any one of embodiments 1 to 14, wherein the Fc region of the fusion protein is galactosylated and sialylated.
16. A polynucleotide encoding the fusion protein of any one of embodiments 1 to 15.
17. The polynucleotide of embodiment 16, wherein the sequence of the polynucleotide has been codon optimized for expressing the fusion protein in a plant.
18. The polynucleotide of embodiment 17, wherein the plant is a tobacco plant.
19. The polynucleotide of embodiment 18, wherein the tobacco plant is *Nicotiana benthamiana.*
20. The polynucleotide of any one of embodiments 16 to 19, wherein the polynucleotide is at least 80%, 85%, 90%, 95%, or 98% identical to any one of SEQ ID NOS:8-10 and 14.

21. An expression vector comprising the polynucleotide of any one of embodiments 16 to 20.
22. The expression vector of embodiment 21, wherein the expression vector comprises a CaMV 35S promoter.
23. The expression vector of embodiment 21, wherein the expression vector comprises an Omega leader sequence of SEQ ID NO: 16.
24. A recombinant cell comprising the polynucleotide of any one of embodiments 16 to 20.
25. The recombinant cell of embodiment 24, wherein the recombinant cell is a plant cell.
26. The recombinant cell of embodiment 25, wherein the plant cell is derived from a tobacco plant.
27. The recombinant cell of embodiment 26, wherein the tobacco plant is *Nicotiana benthamiana*.
28. The recombinant cell of any one of embodiments 24 to 27, wherein the recombinant cell lacks fucosylation and xylosylation pathways and has galactosylation pathways.
29. A plant comprising the recombinant cell of any one of embodiments 24 to 28.
30. The plant of embodiment 29, wherein the plant is a tobacco plant.
31. The plant of embodiment 30, wherein the tobacco plant is *Nicotiana benthamiana*.
32. The plant of any one of embodiments 29 to 31, wherein the plant lacks fucosylation and xylosylation pathways and has galactosylation pathways.
33. A method for producing a fusion protein comprising:
   (a) providing a polynucleotide of any one of embodiments 16 to 20,
   (b) introducing the polynucleotide into a plant tissue, thereby expressing the fusion protein in the plant tissue, and
   (c) recovering the fusion protein from the plant tissue.
34. The method of embodiment 33, wherein the plant tissue expresses a viral RNA gene silencing suppressor.
35. The method of embodiment 33, wherein the polynucleotide is introduced into the plant tissue by *Agrobacterium*.
36. The method of embodiment 35, wherein the polynucleotide is introduced into the plant tissue by vacuum infiltration.
37. The method of embodiment 33, wherein the polynucleotide is introduced into the plant tissue by combining *Agrobacterium* with the plant tissue using transient agroinfiltration to form a mixture and to allow infection of at least one plant cell of the plant tissue, and wherein the fusion protein is recovered from the plant tissue after a period of time sufficient for the plant tissue to transiently express the fusion protein.
38. The method of embodiment 37, wherein the period of time sufficient for the plant tissue to transiently express the fusion protein is at least 3 days, at least 4 days, at least 5 days, or at least 6 days.
39. The method of any one of embodiments 33 to 38, wherein the plant tissue is from a plant that lacks fucosylation and xylosylation pathways and has galactosylation pathways.
40. The method of any one of embodiments 33 to 39, wherein the plant tissue is derived from a tobacco plant.
41. The method of embodiment 40, wherein the tobacco plant is *Nicotiana benthamiana*.
42. A composition comprising the fusion protein of any one of embodiments 1 to 15.
43. The composition of embodiment 42, further comprising a pharmaceutically acceptable carrier or excipient.
44. A method for treating an inflammatory disease in a subject, the method comprising administering to the subject an effective amount of the composition of embodiment 42 or 43.
45. The method of embodiment 44, wherein the inflammatory disease is selected from the group consisting of an inflammatory pulmonary disease, inflammatory vascular disease, inflammatory systemic disease, and inflammation triggered by reperfusion injury.
46. The method of embodiment 45, wherein the inflammatory pulmonary disease is selected from the group consisting of alpha-1 antitrypsin deficiency (AATD), cystic fibrosis (CF), and chronic obstructive pulmonary disease (COPD).

```
INFORMAL SEQUENCE LISTING

SEQ ID NO: 1 (Wild type elafin)
AQEPVKGPVSTKPGSCPIILIRCAMLNPPNRCLKDTDCPGIKKCCEGSCGMACFVPQ SEQ ID NO: 2 (Wild type signal peptide)
MKNTSSLCLLLLVVLCSLTCNSGQA SEQ ID NO: 3 (Linker from human IgG1 hinge region)
EPKSCDKTHT SEQ ID NO: 4 (Wild type Fc)
CPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSPGK SEQ ID NO: 5 (Variant 2 protein sequence; Native form-without any mutation)
MKNTSSLCLLLLVVLCSLTCNSGQAAQEPVKGPVSTKPGSCPIILIRCAMLNPPNRCLKDTDCPGIKKCCEGSCG
MACFVPQEPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVMHEALH
NHYTQKSLSLSPGK SEQ ID NO: 6 (Variant 3 protein sequence, wherein the elafin region
comprises mutations V5G, V9G, M25L, and M51V relative to SEQ ID NO: 1)
MKNTSSLCLLLLVVLCSLTCNSGQAAQEPGKGPGSTKPGSCPIILIRCALLNPPNRCLKDTDCPGIKKCCEGSCG
VACFVPQEPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVMHEALH
NHYTQKSLSLSPGK
```

INFORMAL SEQUENCE LISTING

SEQ ID NO: 7 (Variant 4 sequence, wherein the elafin region comprises
mutations V5G, V9G, M25L, and M51V relative to SEQ ID NO: 1; and wherein the
Fc region comprises mutations M203L and N209S relative to SEQ ID NO: 4)
MKNTSSLCLLLLVVLCSLTCNSGQAAQEPGKGPGSTKPGSCPIILIRCALLNPPNRCLKDTDCPGIKKCCEGSCG
VACFVPQEPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVLHEALH
SHYTQKSLSLSPGK SEQ ID NO: 8 (Variant 2 nucleic acid sequence)
ATGAAGAATACTTCTTCACTTTGTCTTTTGCTTTTGGTTGTTCTTTGTTCATTGACATGCAATTCTGGTCAAGCT
GCTCAGGAACCTGTTAAGGGTCCAGTTTCAACTAAACCTGGATCTTGTCCAATTATTCTTATCAGATGCGCTATG
TTGAATCCTCCAAATAGGTGTTTGAAGGATACAGATTGCCCTGGAATTAAGAAATGTTGCGAAGGTTCATGTGGA
ATGGCTTGCTTTGTTCCTCAAGAGCCAAAGTCTTGTGATAAAACTCATACATGTCCTCCATGCCCTGCTCCAGAG
CTTTTGGGTGGACCTTCTGTTTTTCTTTTTCCTCCAAAGCCAAAAGATACTTTGATGATTTCAAGAACTCCTGAA
GTTACATGCGTTGTTGTTGATGTTTCTCATGAAGATCCAGAGGTTAAGTTTAATTGGTATGTTGATGGTGTTGAG
GTTCATAATGCTAAGACAAAACCAAGAGAAGAGCAATATAATTCAACTTACAGGGTTGTTTCTGTTCTTACAGTT
TTGCATCAGGATTGGCTTAATGGTAAAGAGTACAAGTGTAAAGTTTCAAATAAGGCTTTGCCTGCTCCAATCGAA
AAGACTATTTCTAAGGCTAAAGGACAACCTAGAGAGCCACAGGTTTATACACTTCCTCCATCAAGGGATGAATTG
ACTAAGAACCAAGTTTCTCTTACATGCTTGGTTAAAGGTTTTTACCCTTCAGATATTGCTGTTGAATGGGAGTCT
AATGGTCAGCCAGAAAATAACTATAAGACTACACCTCCAGTTCTTGATTCAGATGGTTCTTTCTTTCTTTACTCA
AAGTTGACTGTTGATAAGTCTAGGTGGCAACAGGGAAATGTTTTCTCTTGTTCAGTTATGCATGAGGCTTTGCAT
AACCATTACACACAGAAGTCTCTTTCATTGTCTCCTGGAAAA SEQ ID NO: 9 (Variant 3 nucleic acid sequence)
ATGAAGAATACTTCTTCACTTTGTCTTTTGCTTTTGGTTGTTCTTTGTTCATTGACATGCAATTCTGGACAAGCT
GCTCAGGAACCTGGAAAGGGACCAGGTTCAACTAAACCTGGTTCTTGTCCAATTATTCTTATCAGATGCGCTCTT
TTGAATCCTCCAAATAGGTGTTTGAAGGATACAGATTGCCCTGGAATTAAGAAATGTTGCGAAGGATCATGTGGT
GTTGCTTGCTTTGTTCCTCAAGAGCCAAAGTCTTGTGATAAAACTCATACATGTCCTCCATGCCCTGCTCCAGAG
CTTTTGGGTGGACCTTCTGTTTTTCTTTTTCCTCCAAAGCCAAAAGATACTTTGATGATTTCAAGAACTCCTGAA
GTTACATGCGTTGTTGTTGATGTTTCTCATGAAGATCCAGAGGTTAAGTTTAATTGGTATGTTGATGGTGTTGAG
GTTCATAATGCTAAGACAAAACCAAGAGAAGAGCAATATAATTCAACTTACAGGGTTGTTTCTGTTCTTACAGTT
TTGCATCAGGATTGGCTTAATGGTAAAGAGTACAAGTGTAAAGTTTCAAATAAGGCTTTGCCTGCTCCAATCGAA
AAGACTATTTCTAAGGCTAAAGGTCAACCTAGAGAGCCACAGGTTTATACACTTCCTCCATCAAGGGATGAATTG
ACTAAGAACCAAGTTTCTCTTACATGCTTGGTTAAAGGATTTTACCCTTCAGATATTGCTGTTGAATGGGAGTCT
AATGGTCAGCCAGAAAATAACTATAAGACTACACCTCCAGTTCTTGATTCAGATGGTTCTTTCTTTCTTTACTCA
AAGTTGACTGTTGATAAGTCTAGGTGGCAACAGGGTAATGTTTTCTCTTGTTCAGTTATGCATGAGGCTTTGCAT
AACCATTACACACAGAAGTCTCTTTCATTGTCTCCTGGAAAA SEQ ID NO: 10 (Variant 4 nucleic acid sequence)
ATGAAGAATACTTCTTCACTTTGTCTTTTGCTTTTGGTTGTTCTTTGTTCATTGACATGCAATTCTGGACAAGCT
GCTCAGGAACCTGGAAAGGGACCAGGTTCAACTAAACCTGGTTCTTGTCCAATTATTCTTATCAGATGCGCTCTT
TTGAATCCTCCAAATAGGTGTTTGAAGGATACAGATTGCCCTGGAATTAAGAAATGTTGCGAAGGATCATGTGGT
GTTGCTTGCTTTGTTCCTCAAGAGCCAAAGTCTTGTGATAAAACTCATACATGTCCTCCATGCCCTGCTCCAGAG
CTTTTGGGTGGACCTTCTGTTTTTCTTTTTCCTCCAAAGCCAAAAGATACTTTGATGATTTCAAGAACTCCTGAA
GTTACATGCGTTGTTGTTGATGTTTCTCATGAAGATCCAGAGGTTAAGTTTAATTGGTATGTTGATGGTGTTGAG
GTTCATAATGCTAAGACAAAACCAAGAGAAGAGCAATATAATTCAACTTACAGGGTTGTTTCTGTTCTTACAGTT
TTGCATCAGGATTGGCTTAATGGTAAAGAGTACAAGTGTAAAGTTTCAAATAAGGCTTTGCCTGCTCCAATCGAA
AAGACTATTTCTAAGGCTAAAGGTCAACCTAGAGAGCCACAGGTTTATACACTTCCTCCATCAAGGGATGAATTG
ACTAAGAACCAAGTTTCTCTTACATGCTTGGTTAAAGGATTTTACCCTTCAGATATTGCTGTTGAATGGGAGTCT
AATGGTCAGCCAGAAAATAACTATAAGACTACACCTCCAGTTTTGGATTCAGATGGTTCTTTCTTTCTTTACTCA
AAGTTGACTGTTGATAAGTCTAGGTGGCAACAGGGTAATGTTTTCTCTTGTTCAGTTCTTCATGAGGCTTTGCAT
TCTCATTATACACAGAAGTCTCTTTCATTGTCTCCTGGAAAA SEQ ID NO: 11 (Elafin nucleic acid sequence codon-optimized for expression
in Pichia pastoris)
GCCCAAGAACCAGTCAAGGGTCCAGTCAGTACAAAGCCAGGTAGTTGCCCAATTATCCTTATTAGATGCGCCATG
TTGAATCCTCCTAACAGATGTTTGAAGGATACTGATTGCCCTGGAATCAAAAAGTGCTGTGAAGGTAGTTGCGGT
ATGGCTTGTTTCGTCCCTCAG SEQ ID NO: 12 (Elafin protein sequence encoded by SEQ ID NO: 11)
AQEPVKGPVSTKPGSCPIILIRCAMLNPPNRCLKDTDCPGIKKCCEGSCGMACFVPQ SEQ ID NO: 13 (Variant 5 protein sequence, wherein the elafin region
comprises mutations V5G, V9G, M25L, and M51V relative to SEQ ID NO: 1;
wherein the Fc region comprises mutations M203L and N209S relative to SEQ
ID NO: 4; and wherein the linker region has a sequence of SEQ ID NO: 15)
MKNTSSLCLLLLVVLCSLTCNSGQAAQEPGKGPGSTKPGSCPIILIRCALLNPPNRCLKDTDCPGIKKCCEGSCG
VACFVPQSSERKCCVECPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGNVFSCSVLHEALHS
HYTQKSLSLSPGK SEQ ID NO: 14 (Variant 5 nucleic acid sequence)
ATGAAAAATACCTCTTCTTTATGTTTGCTCTTGTTGGTGGTGCTCTGCTCTCTCACTTGTAACTCTGGTCAGGCT
GCTCAGGAACCTGGAAAGGGACCTGGTTCTACTAAACCTGGATCATGTCCAATTATTCTTATCAGATGCGCTCTT
TTGAATCCTCCAAATAGGTGTTTGAAGGATACAGATTGCCCTGGTATTAAGAAATGTTGCGAAGGATCTTGTGGT

INFORMAL SEQUENCE LISTING

```
GTTGCTTGCTTTGTTCCACAATCTTCAGAAAGAAAATGTTGCGTTGAGTGTCCTCCATGCCCTGCTCCAGAGCTT
TTGGGTGGACCTTCTGTTTTTCTTTTTCCTCCAAAGCCAAAAGATACTTTGATGATTTCTAGGACTCCTGAAGTT
ACATGTGTTGTTGTTGATGTTTCACATGAAGATCCAGAGGTTAAGTTTAATTGGTATGTTGATGGAGTTGAGGTT
CATAATGCTAAGACAAAACCAAGAGAAGAGCAATATAATTCTACTTACAGGGTTGTTTCAGTTCTTACAGTTTTG
CATCAGGATTGGCTTAATGGTAAAGAATACAAGTGTAAAGTTTCTAATAAGGCTTTGCCTGCTCCAATCGAAAAG
ACTATTTCAAAGGCTAAAGGTCAACCTAGAGAGCCACAGGTTTATACACTTCCTCCATCTAGGGATGAATTGACT
AAGAACCAAGTTTCACTTACATGCTTGGTTAAAGGATTTTACCCTTCTGATATTGCTGTTGAATGGGAGTCAAAT
GGTCAGCCAGAGAATAACTATAAGACTACACCTCCAGTTCTTGATTCTGATGGTTCTTTCTTTCTTTACTCTAAG
TTGACTGTTGATAAGTCAAGATGGCAACAGGGTAATGTTTTCTCTTGCTCAGTTCTCCACGAGGCACTCCATTCA
CATTACACCCAGAAGTCACTCTCTCTCAGTCCAGGAAAA
```

SEQ ID NO: 15 (Linker from human IgG2 hinge region)
SSERKCCVE

SEQ ID NO: 16 (the Q leader sequence, which is modified based on Tobacco mosaic virus (TMV)omega sequence)
TTCAACAATTACCAACAACAACAAACAACAAACAACATTACAATTACTATTTACAATTACAGTCGAAAGGAAGAA
GCC

---

What is claimed is:

1. A fusion protein comprising a secretory signal peptide, an elafin region, a linker, and a Fc region, wherein the fusion protein comprises one or more point mutations in the elafin region relative to SEQ ID NO:1 selected from the group consisting of V5G, V9G, M25L, and M51V, and wherein one of the point mutations is selected from the group consisting of M25L and M51V.

2. The fusion protein of claim 1, wherein the fusion protein is more resistant to proteolytic cleavage and/or oxidation compared to a control fusion protein without the one or more point mutations in the elafin region.

3. The fusion protein of claim 1, wherein the fusion protein comprises the V5G, V9G, M25L, and M51V point mutations in the elafin region.

4. The fusion protein of claim 1, wherein the signal peptide comprises a sequence that is at least 80%, 85%, 90%, 95%, or 98% identical to SEQ ID NO:2.

5. The fusion protein of claim 1, wherein the linker comprises a sequence that is at least 80%, 85%, 90%, 95%, or 98% identical to SEQ ID NO:3 or SEQ ID NO:15.

6. The fusion protein of claim 1, wherein the Fc region comprises a sequence that is at least 80%, 85%, 90%, 95%, or 98% identical to SEQ ID NO:4.

7. The fusion protein of claim 6, wherein the fusion protein comprises one or more point mutations in the Fc region relative to SEQ ID NO:4.

8. The fusion protein of claim 7, wherein the fusion protein has a longer half-life compared to a control fusion protein without the one or more point mutations in the Fc region.

9. The fusion protein of claim 7, wherein the fusion protein comprises one or more point mutations in the Fc region selected from the group consisting of M203L and N209S.

10. The fusion protein of claim 9, wherein the fusion protein comprises the M203L and N209S point mutations in the Fc region.

11. The fusion protein of claim 1, wherein the fusion protein comprises a sequence that is at least 80%, 85%, 90%, 95%, or 98% identical to any one of SEQ ID NOS:5-7 and 13.

12. The fusion protein of claim 1, wherein the Fc region of the fusion protein is galactosylated and sialylated.

13. A composition comprising the fusion protein of claim 1.

14. The composition of claim 13, further comprising a pharmaceutically acceptable carrier or excipient.

* * * * *